United States Patent
Andry et al.

(10) Patent No.: US 10,069,116 B2
(45) Date of Patent: Sep. 4, 2018

(54) CATHODE FOR THIN FILM MICROBATTERY

(71) Applicant: International Business Machines Corporation, Armonk, NY (US)

(72) Inventors: Paul S. Andry, Yorktown Heights, NY (US); Eric P. Lewandowski, White Plains, NY (US); Yu Luo, Hopewell Junction, NY (US); Adinath S. Narasgond, Yonkers, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/789,584

(22) Filed: Oct. 20, 2017

(65) Prior Publication Data
US 2018/0040859 A1 Feb. 8, 2018

Related U.S. Application Data

(62) Division of application No. 14/340,304, filed on Jul. 24, 2014, now Pat. No. 9,806,299.

(51) Int. Cl.
*H01M 2/02* (2006.01)
*C25D 1/04* (2006.01)
(Continued)

(52) U.S. Cl.
CPC ........... *H01M 2/0202* (2013.01); *A61B 5/145* (2013.01); *C25D 1/04* (2013.01); *C25D 1/22* (2013.01); *C25D 5/02* (2013.01); *G02C 7/083* (2013.01); *H01M 4/38* (2013.01); *H01M 4/42* (2013.01); *H01M 4/48* (2013.01); *H01M 4/50* (2013.01); *H01M 4/661* (2013.01); *H01M 4/664* (2013.01); *H01M 10/0436* (2013.01);
(Continued)

(58) Field of Classification Search
CPC ....... H01M 4/50; H01M 4/42; H01M 10/0436
See application file for complete search history.

(56) References Cited

U.S. PATENT DOCUMENTS

| 4,432,937 A | 2/1984 | Kuwayama et al. |
| 4,460,543 A | 7/1984 | Glaeser |

(Continued)

FOREIGN PATENT DOCUMENTS

| EP | 2235773 B1 | 10/2010 |
| GB | 2501801 A | 11/2013 |

(Continued)

OTHER PUBLICATIONS

Liao et al., "A 3μW Wirelessly Powered CMOS Glucose Sensor for an Active Contact Lens", 2011 IEEE International Solid-Slate Circuits Conference; pp. 38-41, 978-1-61284-302-5/11, copyright 2011 IEEE.

(Continued)

*Primary Examiner* — Olatunji Godo
(74) *Attorney, Agent, or Firm* — Scully, Scott, Murphy & Presser, P.C.; Louis J. Percello, Esq.

(57) ABSTRACT

A battery comprising an anode comprising anode material in contact with a metal anode current collector. The battery further comprises a cathode comprising cathode material in contact with a cathode current collector comprising a transparent conducting oxide (TCO). The battery further comprises an electrolyte with a pH in a range of 3 to 7.

15 Claims, 15 Drawing Sheets

(51) Int. Cl.

| | | |
|---|---|---|
| C25D 1/22 | (2006.01) | |
| C25D 5/02 | (2006.01) | |
| G02C 7/08 | (2006.01) | |
| H01M 4/38 | (2006.01) | |
| H01M 4/42 | (2006.01) | |
| H01M 4/48 | (2010.01) | |
| H01M 4/50 | (2010.01) | |
| H01M 4/66 | (2006.01) | |
| H01M 10/04 | (2006.01) | |
| A61B 5/145 | (2006.01) | |
| C25D 3/22 | (2006.01) | |
| C25D 3/54 | (2006.01) | |
| C25D 3/56 | (2006.01) | |
| C25D 5/10 | (2006.01) | |
| C25D 5/50 | (2006.01) | |
| H01M 4/139 | (2010.01) | |
| H01M 4/02 | (2006.01) | |

(52) U.S. Cl.
CPC ........... A61B 2562/028 (2013.01); C25D 3/22 (2013.01); C25D 3/54 (2013.01); C25D 3/56 (2013.01); C25D 3/565 (2013.01); C25D 5/10 (2013.01); C25D 5/50 (2013.01); H01M 4/139 (2013.01); H01M 2002/0205 (2013.01); H01M 2004/027 (2013.01); H01M 2004/028 (2013.01); Y10T 29/49108 (2015.01); Y10T 29/49115 (2015.01)

(56) References Cited

U.S. PATENT DOCUMENTS

| | | | |
|---|---|---|---|
| 4,994,333 | A | 2/1991 | Jose et al. |
| 5,240,793 | A | 8/1993 | Glaeser |
| 5,306,580 | A | 4/1994 | Mansfield, Jr. et al. |
| 5,326,652 | A | 7/1994 | Lake |
| 5,339,024 | A | 8/1994 | Kuo et al. |
| 5,350,645 | A * | 9/1994 | Lake ............... H01M 4/04 29/623.3 |
| 5,376,480 | A | 12/1994 | Shinoda et al. |
| 5,451,766 | A | 9/1995 | Van Berkel |
| 5,558,957 | A | 9/1996 | Datta et al. |
| 5,591,548 | A | 1/1997 | Mao |
| 5,827,621 | A | 10/1998 | Morishita et al. |
| 5,897,522 | A | 4/1999 | Nitzan |
| 6,379,835 | B1 | 4/2002 | Kucherovsky et al. |
| 6,420,071 | B1 | 7/2002 | Lee et al. |
| 6,482,543 | B1 | 11/2002 | Shelekhin et al. |
| 6,540,938 | B1 | 4/2003 | Afzali-Ardakani et al. |
| 6,982,132 | B1 | 1/2006 | Goldner et al. |
| 7,087,348 | B2 | 8/2006 | Holman et al. |
| 7,320,845 | B2 | 1/2008 | Zucker |
| 7,348,096 | B2 | 3/2008 | Schubert et al. |
| 7,435,395 | B2 | 10/2008 | Durkot et al. |
| 7,446,380 | B2 | 11/2008 | Bojarczuk, Jr. et al. |
| 7,491,464 | B2 | 2/2009 | Merrill et al. |
| 7,531,271 | B2 | 5/2009 | Boulton et al. |
| 7,776,468 | B2 | 8/2010 | Richards et al. |
| 7,820,329 | B2 | 10/2010 | Boulton et al. |
| 8,029,927 | B2 | 10/2011 | Tucholski |
| 8,268,475 | B2 | 9/2012 | Tucholski |
| 8,441,411 | B2 | 5/2013 | Tucholski et al. |
| 8,534,831 | B2 | 9/2013 | Tepedino, Jr. et al. |
| 8,586,244 | B2 | 11/2013 | Fensore et al. |
| 8,608,310 | B2 | 12/2013 | Otis et al. |
| 8,637,349 | B2 | 1/2014 | Jenson et al. |
| 8,877,103 | B2 | 11/2014 | Alvarez-Carrigan et al. |
| 8,906,088 | B2 | 12/2014 | Pugh et al. |
| 9,472,789 | B2 | 10/2016 | Andry et al. |
| 9,508,566 | B2 | 11/2016 | Andry et al. |
| 2002/0105092 | A1 | 8/2002 | Coyle |
| 2002/0161404 | A1 | 10/2002 | Schmidt |
| 2003/0099884 | A1 | 5/2003 | Chiang et al. |
| 2003/0165744 | A1 | 9/2003 | Schubert et al. |
| 2005/0048699 | A1 | 3/2005 | Matsunami |
| 2005/0079418 | A1 | 4/2005 | Kelley et al. |
| 2005/0266158 | A1 | 12/2005 | Pokorny et al. |
| 2008/0187824 | A1 | 8/2008 | Tomantschger |
| 2008/0248382 | A1 | 10/2008 | Sastry et al. |
| 2009/0108440 | A1 | 4/2009 | Meyer et al. |
| 2010/0068617 | A1 | 3/2010 | Bedjaoui et al. |
| 2010/0285372 | A1 | 11/2010 | Lee et al. |
| 2010/0310932 | A1 | 12/2010 | Martin et al. |
| 2011/0048781 | A1 | 3/2011 | Neudecker et al. |
| 2011/0097623 | A1 | 4/2011 | Marinis, Jr. et al. |
| 2011/0100458 | A1 | 5/2011 | Kang et al. |
| 2011/0162972 | A1 | 7/2011 | Furuya et al. |
| 2011/0163812 | A1 | 7/2011 | Bansal et al. |
| 2011/0311857 | A1 | 12/2011 | Tucholski |
| 2012/0140167 | A1 | 6/2012 | Blum |
| 2012/0236254 | A1 | 9/2012 | Pugh et al. |
| 2013/0035760 | A1 | 2/2013 | Portney |
| 2013/0108907 | A1 | 5/2013 | Bhardwaj et al. |
| 2013/0122132 | A1 | 5/2013 | Pugh et al. |
| 2013/0174978 | A1 | 7/2013 | Pugh et al. |
| 2013/0203895 | A1 | 8/2013 | Dershem |
| 2013/0222759 | A1 | 9/2013 | Pugh et al. |
| 2013/0230774 | A1 | 9/2013 | Ortega et al. |
| 2013/0258277 | A1 | 10/2013 | Pugh et al. |
| 2014/0000101 | A1 | 1/2014 | Pugh et al. |
| 2014/0028969 | A1 | 1/2014 | Pugh et al. |
| 2014/0085599 | A1 | 3/2014 | Etzkorn |
| 2014/0107445 | A1 | 4/2014 | Liu |
| 2014/0320800 | A1 | 10/2014 | Collins et al. |
| 2014/0340631 | A1 | 11/2014 | Pugh |
| 2014/0346695 | A1 | 11/2014 | Pugh et al. |
| 2014/0349211 | A1 | 11/2014 | Wei et al. |
| 2014/0354946 | A1 | 12/2014 | Pugh et al. |
| 2015/0029424 | A1 | 1/2015 | Gordon et al. |
| 2015/0288024 | A1 | 10/2015 | Andry et al. |
| 2015/0323811 | A1 | 11/2015 | Flitsch et al. |
| 2016/0045144 | A1 | 2/2016 | Bansal et al. |

FOREIGN PATENT DOCUMENTS

| | | |
|---|---|---|
| JP | 2006274346 A | 10/2006 |
| NO | 2011113903 A1 | 9/2011 |
| WO | 2008091859 A1 | 7/2008 |
| WO | 2013062662 A1 | 5/2013 |

OTHER PUBLICATIONS

Rolka et al., "Integration of a Capacitive EIS Sensor into a FIA System for pH and Penicillin Determination", 2 Sensors, ISSN 1424-8220; Copyright 2004 by MDPI; Sensors 2004, 4; pp. 84-94, website: <http://www.mdpi.net/sensors>.

Badugu et al.; "A Glucose Sensing Contact Lens: A Non-Invasive Technique for Continuous Physiological Glucose 3 Monitoring", Journal of Fluorescence, Sep. 2003, pp. 371-374, vol. 13, No. 5.

Beeckman, et al., "Liquid-crystal photonic applications", SPIEDigitallibrary.org/oe, Optical Engineering, Aug. 2011, vol. 50(8), 1 081202, http://opticalengineering.spiedigitallibrary.org/ on04/07/2014, Terms of Use: http://spiedl.org/terms.

Blue Spark Technologies, "UT Series Printed Batteries", Product Information, UT Series Oct-12-2, Copyright 2012, website: <www.bluesparktechnologies.com>.

Ding Ke-Qiang, "Cyclic Voltmmetrically-prepared MnO2 Coated on a ITO Glass Substrate", Journal of the Chinese Chemical Society; 2009; pp. 171-181, 56.

Li, Xiaoping et al., "Composite of Indium and Polysorbale 20 as Inhibitor for Zinc Corrosion in Alkaline Solution", Bull. Korean Chem. Soc.; 2012; vol. 33; No. 5.; <http:i/dx.doi.org/10.5012/bkcs.2012.33.5.1566>.

Ren, Hongwen et al., "Tunable electronic lens using a gradient polymer network liquid crystal", Applied Physics Letters, Jan. 6, 2003, vol. 82, No. 1.

Provisional U.S. Appl. No. 61/858,346, filed Jul. 25, 2013 entitled "Variable Focal Length Lens".

(56) References Cited

OTHER PUBLICATIONS

Provisional U.S. Appl. No. 61/976,595, filed Apr. 8, 2014 entitled "Thin Flexible Microsystem with Low-Profile Integrated Thin Film Battery".
List of IBM Patents or Patent Applications Treated as Related Dated Oct. 20, 2017, 2 Pages.

* cited by examiner

US 10,069,116 B2

CATHODE FOR THIN FILM MICROBATTERY

BACKGROUND OF THE INVENTION

The present invention relates generally to the field of microsystem architectures and more particularly to a structure and composition of a cathode in a thin film flexible microbattery.

A synergy of advances in materials science, microfabrication technology, biological micro-electro-mechanical systems (bioMEMS), microfluidics, and microelectronics has fueled a rapid growth of the capabilities and applications of microsystems. For example, the advancing capabilities of microsystems with an increasingly mature understanding of biological processes have a potential to significantly advance the quality of healthcare. Tiny tissue-integrated microsystems that enhance or monitor biological functions (e.g., for diabetics) and can operate for months or years at a time are envisioned. Such integrated devices must be biocompatible, neurologically and cosmetically comfortable, and effective—and with excellent reliability and longevity, especially if surgically implanted or if responsible for life-critical functions. To achieve widespread application, they must be commercially viable and cost effective.

SUMMARY

Embodiments of the present invention disclose a battery, comprising an anode comprising anode material in contact with a metal anode current collector. The battery also comprises a cathode comprising cathode material in contact with a cathode current collector comprising a transparent conducting oxide (TCO). The battery also comprises an electrolyte with a pH in a range of 3 to 7. Embodiments of the present invention also disclose a method for forming a battery. The method includes fabricating a cathode in a first cavity in a first dielectric element. The method further includes fabricating an anode in a second cavity in a second dielectric element. The method further includes joining the cathode and the anode in a complanate manner.

DETAILED DESCRIPTION

Figure 1:
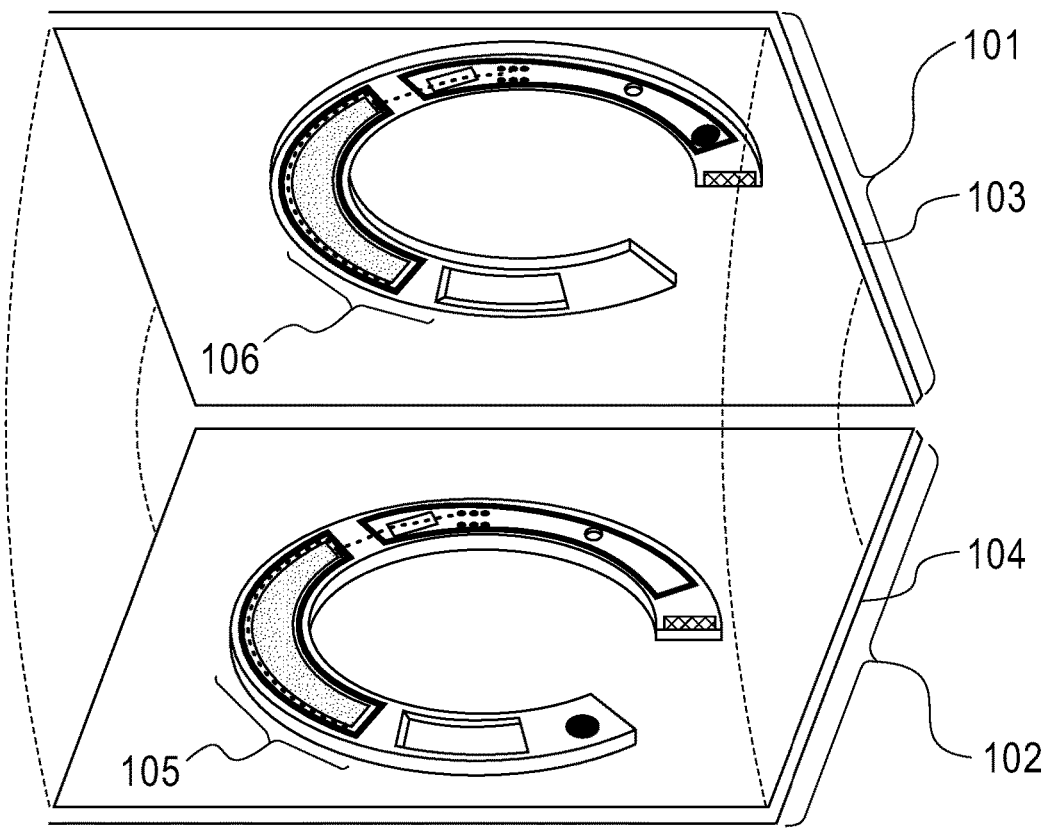
FIG. 1 is a diagram that shows two sides of a microsystem during fabrication in accordance with an embodiment of the present invention.

Detailed embodiments of the present invention are disclosed herein with reference to the accompanying drawings. It is to be understood that the disclosed embodiments are merely illustrative of potential embodiments of the present invention and may take various forms. In addition, each of the examples given in connection with the various embodiments is intended to be illustrative, and not restrictive. Further, the Figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the disclosed present invention, as oriented in the drawing Figures. The terms "overlying", "underlying", "atop", "on top", "positioned on" or "positioned atop" mean that a first element, such as a first structure, is present on a second element, such as a second structure, wherein intervening elements, such as an interface structure may be present between the first element and the second element. The term "direct contact" means that a first element, such as a first structure, and a second element, such as a second structure, are connected without any intermediary conducting, insulating or semiconductor layers at the interface of the two elements.

Contact lenses are potentially an excellent microsystem platform for a multitude of general diagnostic and vision-related functions. However, microsystems that are integrated into a contact lens or an ocular environment (e.g., a corneal implant) to perform ophthalmological functions have constraints in addition to those associated with integration into other types of human tissue—a microsystem must have extremely small dimensions, and be thin and flexible. The quest for such materials that are both amenable to economic fabrication and have the requisite optical, electrical and biological properties are currently an active area of research.

A microsystem that is suitable for integration into a contact lens, which includes an energy source and accommodates a variety of bioMEM and microelectronic mechanisms and that is realizable with economic microfabrication technologies is beneficial. A variety of health-related augmentation, diagnostic, and monitoring functions could potentially be hosted in such an ecosystem, greatly decreasing individual development times and costs.

A need for energy is a common requirement of active microsystems. An energy requirement may be minimal in many situations thus enabling a microbattery to provide ample energy for a microsystem. For example, a microbattery may be efficacious for a system embedded in a contact lens. However, batteries often contain substances that are toxic to humans, may be dimensionally awkward, and are opaque and inflexible, so compatible battery technologies are sought for ophthalmological devices.

In an embodiment of the present invention, a microsystem that can serve as a platform and ecosystem for a variety of microsystems and that can be implanted into human tissue is presented. In an embodiment, the microsystem is fabricated, using well-known processes, in two halves, a top side and a bottom side, that are joined after the two halves are fabricated. Each side is individually fabricated in a "C" shape, after which the top side is aligned with and superimposed over the bottom side and joined with the bottom side. An arc shaped gap in a resulting "C" shape that is comprised of the top side superimposed on the bottom side, is forced to close, forming an annulus.

In an embodiment, the microsystem includes one or more thin silicon die, interconnect wiring, and a battery energy source that is composed of materials that are benign, thin, and flexible. One or more circuits and memories are customized on the one or more silicon die to perform one or more functions. The one or more circuits may be quantum, electrical, chemical, optical, mechanical, electromagnetic, microfluidic, biological, or a combination thereof. In an embodiment the microsystem can be incorporated into a contact lens with a periphery of an annulus of the microsystem aligning with a periphery of the contact lens and the center of the annulus aligning with a center of the contact lens. In another embodiment, the microsystem is embedded in a corneal implant.

The present invention will now be described in detail with reference to the Figures, in accordance with an embodiment of the present invention.

FIG. 1 depicts microsystem assembly 100 that, in an embodiment, consists of two microassembly planars, microassembly top planar 101 and microassembly bottom planar 102. Microassembly top planar 101 includes microsystem top component 106 on temporary support wafer 103 and microassembly bottom planar 102 includes microsystem bottom component 105 on temporary support wafer 104. In an embodiment microsystem top component 106 and microsystem bottom component 105, are two sides of a single microsystem that are joined to form a unified microsystem during a fabrication process. Temporary support wafers 103 and 104 are removed after the two sides are joined during a fabrication process.

In an embodiment, a side of a battery, a cathode side, is fabricated in microsystem top component 106 and the other side of the battery, an anode side, is fabricated in microsystem bottom component 105. In another embodiment, the anode side is fabricated in microsystem top component 106 and the cathode side is fabricated in microsystem bottom component 105. The cathode side of the battery and the anode side of the battery are superimposed and joined when the two halves of the single microsystem are joined.

Figure 2:
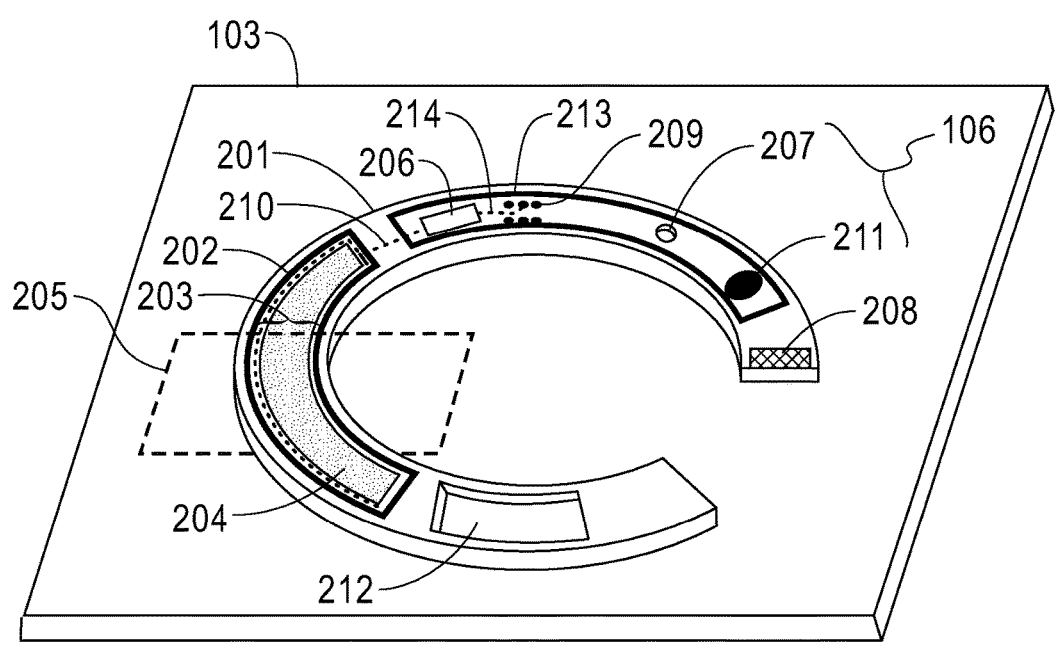
FIG. 2 is a diagram that shows a top side of a microsystem that contains a portion of a microbattery in the microsystem during fabrication in accordance with an embodiment of the present invention.

FIG. 2 depicts microassembly top planar 101 in more detail. In an embodiment, a position of components on microassembly bottom planar 102 is substantially similar to a position of components on microassembly top planar 101. Those skilled in the art understand that a position of components on microassembly bottom planar 102 can be different from a position of components on microassembly top planar 101.

In an embodiment, top polymer flex substrate 201 is a flex polymer material, e.g., polyethylene, or Kapton® (Kapton® is a registered trademark of DuPont Corporation), that is deposited on temporary support wafer 103 to provide a support matrix material for a creation of one or more structures in microsystem top component 106. Cavity 212 is etched into top polymer flex substrate 201 to accommodate a possible protuberance caused by one or more dies and pads on microsystem bottom component 105 to enable microsystem top component 106 to be joined with microsystem bottom component 105 in a complanate manner. The term complanate is defined as "made level" and as "put into or on one plane".

Cavity 203 is etched into polymer flex substrate 201 to accommodate battery material 204 and polymer bondable seal material 202. In an embodiment, an etching of cavity 203 is accomplished by masking a photoresist in combination with reactive-ion etching (RIE). RIE is an etching technology that uses chemically reactive plasma to remove material deposited on wafers. In other embodiments the etching is accomplished by using a metal mask and a laser. Those skilled in the art understand there are many ways to etch cavity 203 and that polymer bondable seal material 202 is a photopatterned polymer bondable seal material that is photo-definable.

In an embodiment, rabbet joint adhesive 208 adheres to a substantially similar rabbet joint adhesive on microsystem bottom component 105 (rabbet joint adhesive 308 in FIG. 3) to bond the ends of a microsystem in a "C" or arc shape together into a shape of a closed annulus. In an embodiment, rabbet joint adhesive 208 and 308 are polymer adhesives that bond when placed in contact with each other and cured using pressure, or heat, or UV, or a combination thereof. In an embodiment, rabbet joint adhesive 208 and 308 are electrically conductive to form an electrical as well as a mechanical connection. A rabbet joint is a common carpentry joint in which a recess is formed on a first item and on a second item to be joined by the rabbet joint, such that a recess on a first item fits into a protuberance on a second item and a protuberance on the first item fits into a recess on the second item.

Silicon die 206 is a processing and/or memory element that is operable on quantum, electrical, chemical, optical, mechanical, microfluidic, electromagnetic, or biological principles and phenomena, or a combination thereof that provides a customizable functionality to an assembled microsystem. In an embodiment, one or more silicon dies substantially similar to silicon die 206 are attached to top polymer flex substrate 201. In an embodiment, silicon die 206 is between 20 µm and 100 µm in thickness.

Polymer bondable seal material 213 seals a portion of a surface of microsystem top component 106. Those skilled in the art understand that polymer bondable seal material 213 is a photopatterned polymer bondable seal material. Wiring trace 210 is an electrical conductor from battery material 204 to silicon die 206. Pads 209 are electrical contacts that provide electrical connections to silicon die 206 via wiring trace 214. In an embodiment, wiring trace 210 and wiring trace 214 are comprised of indium tin oxide (ITO) on a blend of titanium and tungsten (TiW). In an embodiment, hole 207 provides a path for one or more connective wires from pads 209 to one or more mechanisms that are external to microsystem top component 106. Conductive adhesive 211 adheres to a substantially similar conductive adhesive on microsystem bottom component 105 to bond microsystem top component 106 with microsystem bottom component 105. Conductive adhesive 211 is an electrical conductor and, in an embodiment, provides for an electrical connection between microsystem top component 106 and microsystem bottom component 105. In an embodiment, the electrical connection enables one or more batteries in a microsystem to be connected in series or parallel and/or enables signals to propagate between two or more locations in the microsystem.

In an embodiment, plane 205 depicts a cross-sectional view of a cathode side of a microbattery, the fabrication of which is discussed in reference to FIGS. 7 through 11 and FIGS. 20 and 21.

Figure 3:
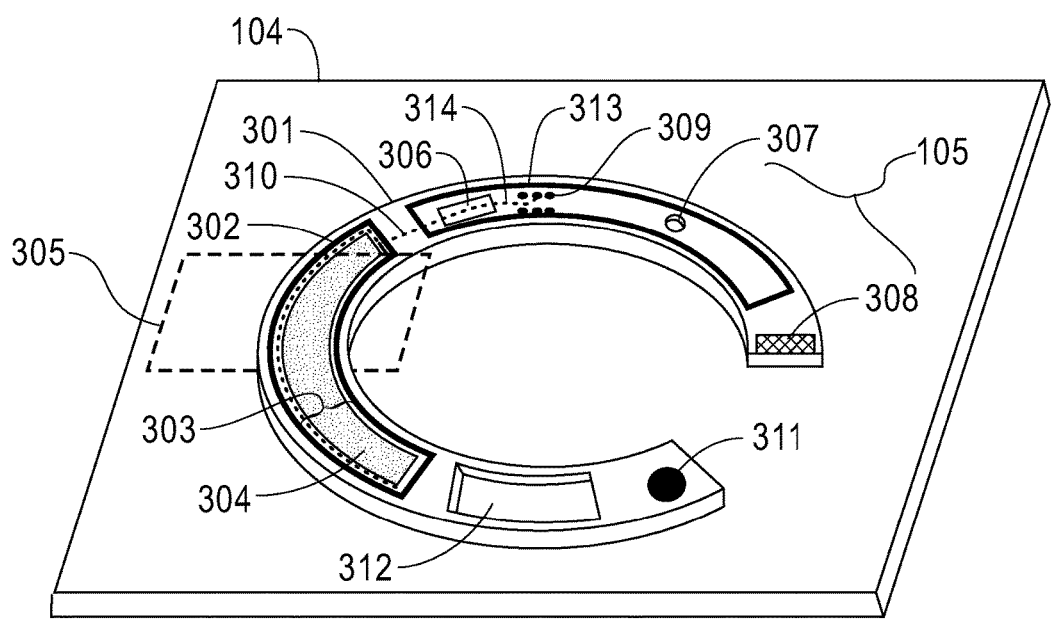
FIG. 3 is a diagram that shows a bottom side of a microsystem that contains a portion of a microbattery in the microsystem during fabrication in accordance with an embodiment of the present invention.

FIG. 3 depicts microassembly bottom planar 102 in more detail. In an embodiment, a position of components on microassembly bottom planar 102 is substantially similar to a position of components on microassembly top planar 101. Those skilled in the art understand that a position of components on microassembly bottom planar 102 can be substantially different from a position of components on microassembly top planar 101.

In an embodiment, bottom polymer flex substrate 301 is a flex polymer material, e.g., Kapton® or polyethylene, which is deposited on temporary support wafer 104 to provide structural support for microsystem bottom component 105. Cavity 312 is etched into bottom polymer flex substrate 301 to accommodate a protuberance caused by silicon die 206 and pads 209 on microsystem top component 106 so that microsystem top component 106 can be joined with microsystem bottom component 105 in a complanate manner.

Cavity 303 is etched into bottom polymer flex substrate 301 to accommodate battery material 304 and polymer bondable seal material 302. In an embodiment, an etching of cavity 303 can be accomplished with photoresist in combination with reactive-ion etching. In other embodiments, the etching is accomplished with a metal mask and a laser. Those skilled in the art understand that there are many ways to etch cavity 303 and that polymer bondable seal material 302 is a photopatterned polymer bondable seal material that is photo-definable. In an embodiment, rabbet joint adhesive 308 adheres to rabbet joint adhesive 208 on microsystem top component 106 to bond the ends of a microsystem in a "C" or arc shape together into a shape of a closed annulus.

Silicon die 306 is a processing and/or memory element that is operable on quantum, electrical, chemical, optical, mechanical, microfluidic, electromagnetic, or biological principles and phenomena, or a combination thereof that provides a customizable functionality to an assembled microsystem. In an embodiment, one or more silicon dies substantially similar to silicon die 306 are attached to bottom polymer flex substrate 301. In an embodiment, silicon die 306 is between 20 μm and 100 μm in thickness.

Polymer bondable seal material 313 seals a portion of a surface of microsystem bottom component 105. Those skilled in the art understand that polymer bondable seal material 313 is a photopatterned polymer bondable seal material that is photo-definable. Wiring trace 310 is an electrical conductor from battery material 304 to silicon die 306. In other embodiments, a plurality of wiring traces distributes energy to energy consuming components such as silicon die 306. Pads 309 are electrical contacts that provide electrical connections to silicon die 306 via wiring trace 314. In an embodiment, wiring trace 310 and wiring trace 314 are comprised of indium tin oxide (ITO) on a blend of titanium and tungsten (TiW). In an embodiment, hole 307 provides a path for one or more connective wires from pads 309 to one or more mechanisms that are external to microsystem bottom component 105. Conductive adhesive 311 adheres to conductive adhesive 211 on microsystem top component 106 to bond microsystem top component 106 with microsystem bottom component 105. Conductive adhesive 311 is an electrical conductor and in an embodiment, provides for an electrical connection between microsystem top component 106 and microsystem bottom component 105. In an embodiment, the electrical connection enables one or more batteries in a microsystem to be connected in series or parallel and enables signals to propagate between two or more locations in a microsystem.

In an embodiment, plane 305 depicts a cross-sectional view of an anode side of a microbattery, the fabrication of which is discussed in reference to FIGS. 12 through 21.

Figure 4:
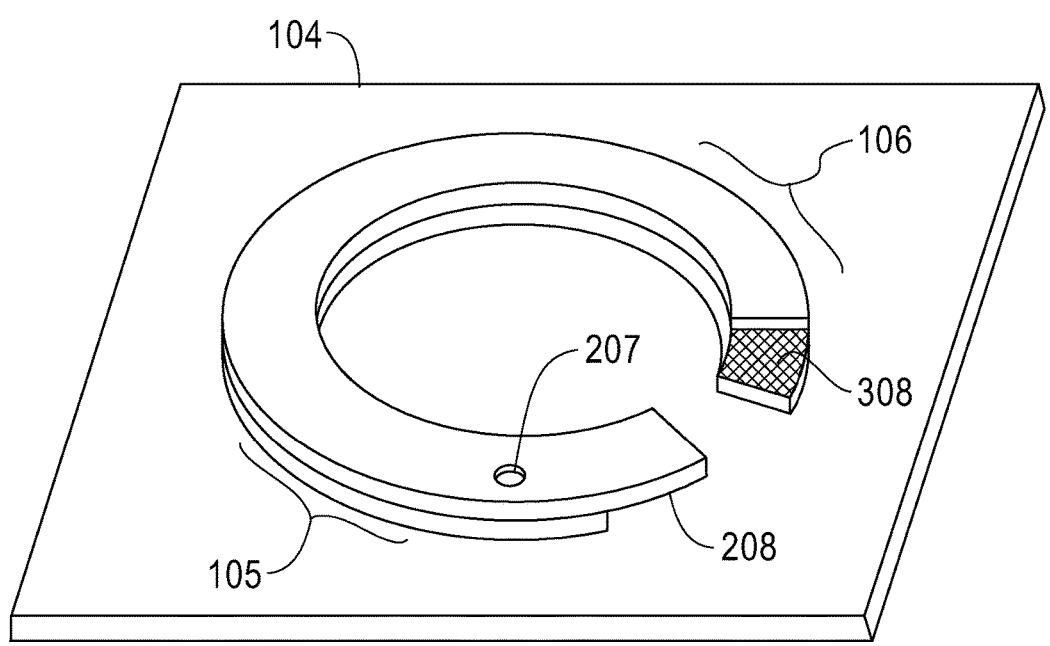
FIG. 4 is a diagram that shows a positioning of a top side of a microsystem that is free of its handler over a bottom side of the microsystem that is still attached to its handler during fabrication in accordance with an embodiment of the present invention.

FIG. 4 depicts microsystem top component 106, with temporary support wafer 103 removed, aligned and bonded with microsystem bottom component 105 on microassembly bottom planar 102 with conductive adhesive 211 adhering to conductive adhesive 311.

Figure 5:
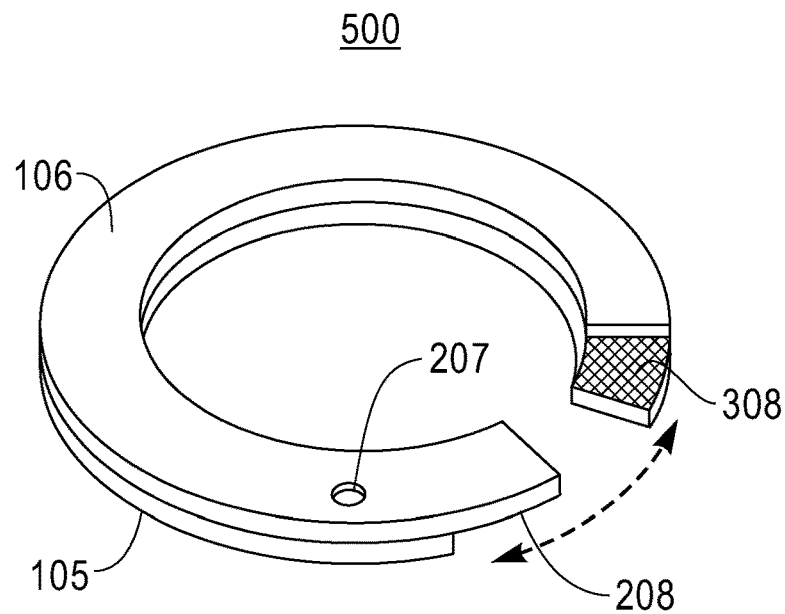
FIG. 5 is a diagram that shows a positioning of a top side of a microsystem that is free of its handler over a bottom side of the microsystem that is free of its handler, before a rabbet joint is closed in accordance with an embodiment of the present invention.

FIG. 5 depicts microsystem top component 106, aligned and bonded with microsystem bottom component 105 with temporary support wafer 104 removed. Rabbet joint adhesive 308 on microsystem bottom component 105 is in a position to bond with rabbet joint adhesive 208 on microsystem top component 106 when the ends of "C" shaped microsystem 500 are joined and bonded together. In an embodiment, rabbet joint adhesive 208 and 308 are electrically conductive to form an electrical as well as a mechanical contact.

Figure 6:
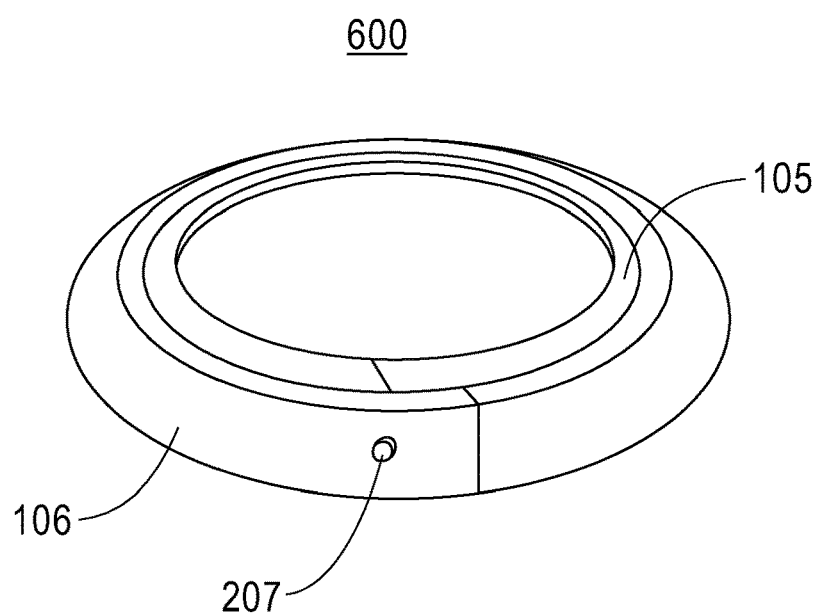
FIG. 6 depicts the microsystem in FIG. 5 after the rabbet joint is closed in accordance with an embodiment of the present invention.

FIG. 6 depicts microsystem 600 that is "C" shaped microsystem 500 after a gap in the "C" shaped microsystem 500 is closed by a bonding of rabbet joint adhesive 308 on microsystem bottom component 105 with rabbet joint adhesive 208 on microsystem top component 106. A closing of the gap in "C" shaped microsystem 500 compresses a material on an inside of the "C" and stretches a material on an outside of the "C", causing the material on the inside to buckle upward relative to material on an outside of the "C", resulting in a conical shape to an upper surface of an annulus. In an embodiment, a curvature of the upper surface of the annulus conforms generally to a curvature of a convex outer surface of a concavo-convex shaped contact lens, enabling microsystem 600 to be efficaciously embedded in the contact lens. If embedded in a contact lens, microsystem 600 capacitates vision through a central circular "donut" hole in the conical shaped annulus that is a shape of microsystem 600. The flexibility of microsystem 600 enables it to be transformed from the planar shape of microsystem 500 into the conical shape of microsystem 600 by squeezing the gap in "C" shaped microsystem 500 together. This shape transformation could not be accomplished if micro system 500 was rigid with little or no flexibility. The flexibility of microsystem 500 is defined by a radius of curvature of between about 4 mm and about 20 mm.

Embodiments of the present invention recognize that microsystem 600 is capable of being incorporated into a contact lens. If microsystem 600 is incorporated into a contact lens, its shape and dimensions are defined by the shape of the human eye. The inner radius of the cone shape achieved after closing the gap in "C" shaped microsystem 500 is constrained by the need to have a sufficient visual opening. A minimum radius of about 3 mm for the inner radius is practical, and a larger radius is desirable. The outer radius of the cone shape is limited by the size of the cornea and the contact lens material around the cone shape of microsystem 600. The outer radius is less than about 9 mm.

The cone slope (as measured from the central axis of the cone) is a function of the inner and outer radii and is fabricated so that the cone slope approximates the slope of the eye surface between the inner and outer radius, within a range that is bounded by the contact lens thickness. Desired cone surface angles depend the range of eye dimensions that are envisioned as application targets for microsystem 600. If a corneal radius of curvature is R (about 8 mm), then for an inner cone radius of ri and outer cone radius of ro, a reasonable median cone angle A, is determined using Formula (1).

$$A = \arctan\left\{\frac{\sqrt{R^2 - ri^2} - \sqrt{R^2 - ro^2}}{ro - ri}\right\} \quad \text{Formula (1)}$$

This is the angle between a surface of a cone and a central axis of the cone. The central axis of the cone is also collinear with the radius of a sphere (e.g., an eye) that the cone penetrates with the apex of the cone at the center of the sphere. The cone angle can be adjusted from cone angle A if the contact lens is not spherical. Typical cone angles are likely to be between about 15 and about 40 degrees. A cone thus described can be cut and flattened into a flat arc of inner radius ri/cos A, outer radius ro/cos A, and with an arc angle, cos A*360 degrees.

In an embodiment, microsystem 600 incorporates a microbattery to provide energy for one or more functions realized in microsystem 600. In an embodiment, a cathode of a microbattery is fabricated on microsystem top component 106 and an anode of the microbattery is fabricated on microsystem bottom component 105. The completed microbattery is formed when the cathode is placed in contact with the anode during a fabrication process.

In an embodiment, microsystem 600 comprises one or more of the following: one or more thermal, pressure, chemical, and biochemical sensors; one or more medicine delivery mechanisms for release and/or controlled release of liquids and/or bioactive chemicals, one or more light based sensors, indicators and/or displays; one or more radio frequency, visible light, infrared, and audio transmitters and/or receivers. In an embodiment, micro system 600 comprises one or more tactile indicators, vibrators, photonic, particle, image, and/or tactile sensors. In an embodiment, microsystem 600 is embedded in a contact lens or is a corneal implant wherein microsystem 600 enhances and/or enables vision. In an embodiment, microsystem 600 is embedded in a contact lens and adjusts a focal length of the contact lens using an electro-optical mechanism on microsystem 600 or controlled by microsystem 600. Examples of an electro-optical mechanism are described in U.S. Patent Publication No. 2015/0029424 filed concurrently with this application, the entirety of which is incorporated by reference herein. In an embodiment, microsystem 600 comprises a heating element. In an embodiment, microsystem 600 comprises a microfluidic or micromechanical mechanism such as a gyroscope or motion sensor. In an embodiment, microsystem 600 comprises a scene, and/or facial, and/or movement (e.g., gate) recognition mechanism. In an embodiment, microsystem 600 is embedded in each of two contact lenses, one contact lens in each of two eyes, and a microsystem 600 in a contact lens in an eye communicates with another microsystem 600 that is in another contact lens that is in another eye of a same person or in an eye of another person.

Figure 7:
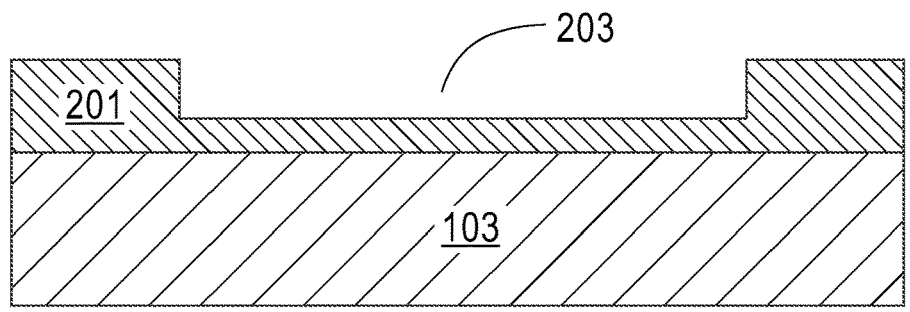
FIG. 7 depicts a sectional view through the plane of FIG. 2 that shows a cavity that is etched to accommodate cathode material during a fabrication of the cathode side of a microbattery in accordance with an embodiment of the present invention.

FIGS. 7-11 depict a cathode side of the microbattery, transected by plane 205 of FIG. 2, at different steps during a fabrication process, in accordance with an embodiment of the present invention. FIG. 7 shows cavity 203 etched into top polymer flex substrate 201 that is deposited on temporary support wafer 103 to accommodate cathode material in the first step. In an embodiment, temporary support wafer 103 is made of glass.

Figure 8:
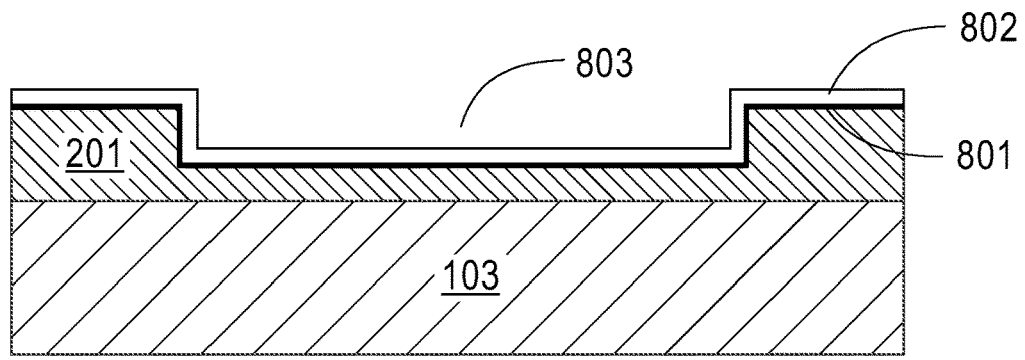
FIG. 8 depicts a sectional view through the plane of FIG. 2 that shows a layer of a cathode-compatible current collector conductor over an adhesion metal layer in the cavity shown in FIG. 7 during a fabrication of the cathode side of the microbattery in accordance with an embodiment of the present invention.

FIG. 8 shows a next step in which an adhesion metal layer 801 and a layer of transparent conducting oxide 802 are deposited as a layer in cavity 203 creating layered cavity 803 and over a surface of top polymer flex substrate 201. In an embodiment, adhesion metal layer 801 is titanium tungsten (TiW), however, those skilled in the art understand that titanium (Ti) or tantalum (Ta) or other suitable material can be used in place of TiW. In an embodiment, adhesion metal layer 801 serves as a metal barrier to prevent electrolyte egress from the cathode of the battery. In an embodiment, adhesion metal layer 801 serves as an electrical contact to the battery. In an embodiment, adhesion metal layer 801 has discontinuities to electrically isolate a mechanical seal bonded to adhesion metal layer 801 from a battery electrical circuit.

In an embodiment, transparent conducting oxide 802 is indium tin oxide (ITO), however, those skilled in the art understand that other transparent conducting oxides can be used, such as indium zinc oxide (IZO), Al-doped zinc oxide (AZO), or Ga-doped zinc oxide (GZO). Transparent conducting oxide 802 serves as a cathode current collector. In an embodiment, a combination of ITO, IZO, AZO, and GZO can be used. In an embodiment, transparent conducting oxide 802 can be replaced with titanium (Ti), gold (Au), carbon-coated Ti or carbon-coated Au. In an embodiment, transparent conducting oxide 802 can be thin, with a thickness of between 20 nm and 200 nm, which provides for a mechanically flexible battery and consumes less space than a material requiring a thicker layer for the cathode current collector. A mechanically flexible battery facilitates a use of the battery in a system that can conform to a biological shape in a living tissue, for example. In an embodiment, the battery has a flexibility defined by a radius of curvature of between about 4 mm and 20 mm.

Figure 9:
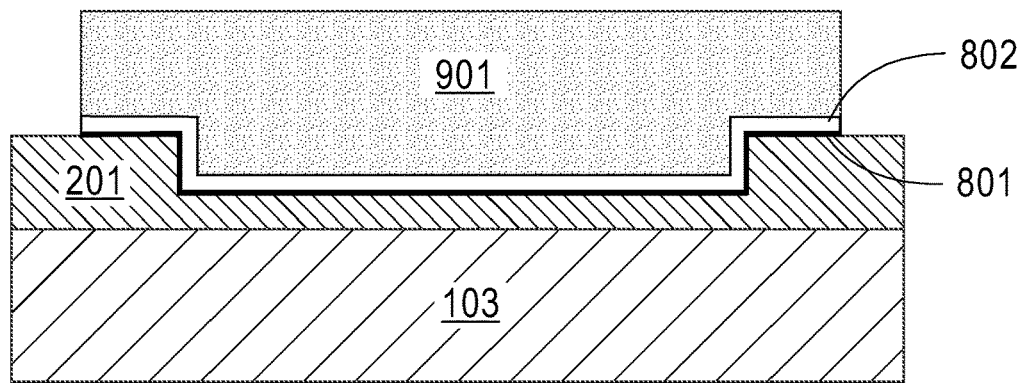
FIG. 9 depicts a sectional view through the plane of FIG. 2 that shows a layer of photoresist deposited over the cathode-compatible current collector conductor in the cavity shown in FIG. 8 during a fabrication of the cathode side of the microbattery in accordance with an embodiment of the present invention.

FIG. 9 shows a next step in a fabrication of the cathode in which a layer of photoresist 901 is deposited over transparent conducting oxide 802, completely fills layered cavity 803 and forms a layer of photoresist 901 over top polymer flex substrate 201. A patterning of photoresist 901 defines wiring trace 210 and wiring trace 214 and a pattern of transparent conducting oxide 802 and adhesion metal layer 801. In a subtractive etching process, unmasked areas of transparent conducting oxide 802 and adhesion metal layer 801 are removed. In other embodiments, a plurality of wiring traces are defined to meet a requirement of microsystem 600.

Figure 10:
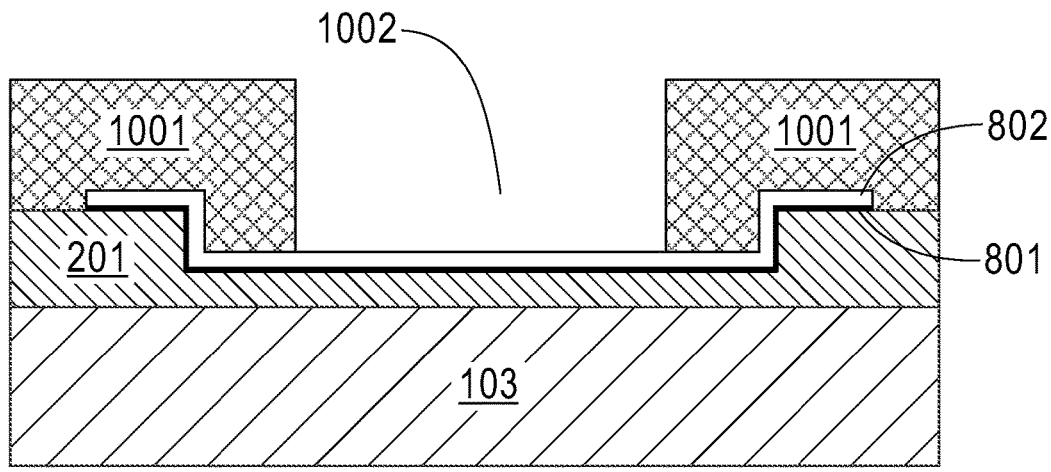
FIG. 10 depicts a sectional view through the plane of FIG. 2 after a polymer bondable seal material is applied and patterned, exposing the cathode-compatible current collector conductor, the cathode current collector, during a fabrication of the cathode side of a microbattery in accordance with an embodiment of the present invention.

FIG. 10 shows a next step in a fabrication of the cathode in which photoresist 901 is completely stripped and polymer bondable seal material 1001 is applied and patterned, creating cavity 1002 and exposing a surface of transparent conducting oxide 802, which is the cathode current collector. Polymer bondable seal material 1001 that is left after etching to create cavity 1002 is permanent and is not stripped. Polymer bondable seal material 1001 is polymer bondable seal material 202, of FIG. 2, viewed from a different perspective.

Figure 11:
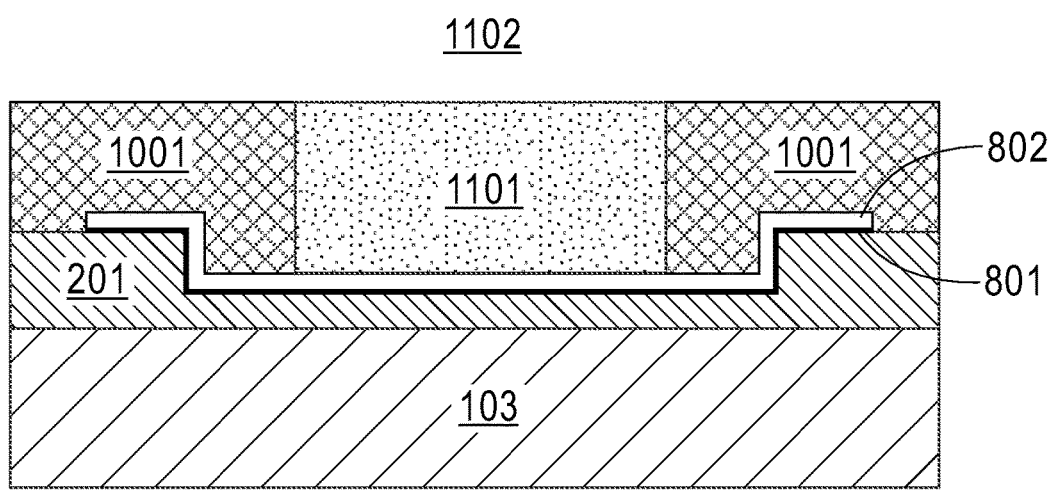
FIG. 11 depicts a sectional view through the plane of FIG. 2 that shows a cathode material inserted over the cathode-compatible current collector conductor during a fabrication of the cathode side of the microbattery in accordance with an embodiment of the present invention.

FIG. 11 shows a step in a fabrication of the cathode side of the battery in which cathode material 1101 is inserted into cavity 1002 forming cathode side 1102 of the battery. In an embodiment, cathode material 1101 is manganese dioxide (MnO2), however, those skilled in the art understand that other suitable materials can be used. Cathode material 1101 can be electroplated nickel hydroxide (NiOOH) or a mixture of MnO2 with or without binder. Because transparent conducting oxide 802 is thin, less space is consumed by transparent conducting oxide 802, leaving more space for cathode material 1101, enabling a construction of a battery that contains more energy relative to a battery of a same size that uses a thicker material for a cathode current collector. In an embodiment, cathode material 1101 is in direct contact with transparent conducting oxide 802, a current collector.

Having described embodiments of a cathode (which are intended to be illustrative and not limiting), it is noted that modifications and variations may be made by persons skilled in the art in light of the above teachings. It is therefore to be understood that changes may be made in the particular embodiments disclosed which are within the scope of the present invention as outlined by the appended claims.

Figure 12:
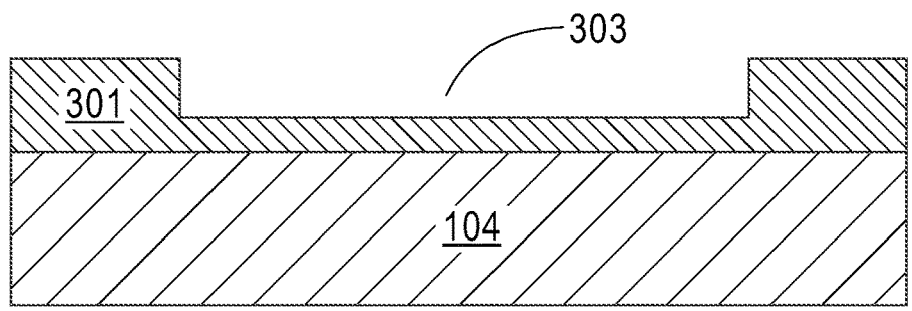
FIG. 12 depicts a sectional view through the plane of FIG. 3 that shows a cavity that is etched to accommodate anode material during a fabrication of the anode side of a microbattery in accordance with an embodiment of the present invention.

FIGS. 12-19 depicts an anode side of the microbattery transected by plane 305 of FIG. 3 at different steps during a fabrication process, in accordance with an embodiment of the present invention. FIG. 12 shows cavity 303 etched into bottom polymer flex substrate 301 that is deposited on temporary support wafer 104 to accommodate anode material in the first step. In an embodiment, temporary support wafer 104 is made of glass.

Figure 13:
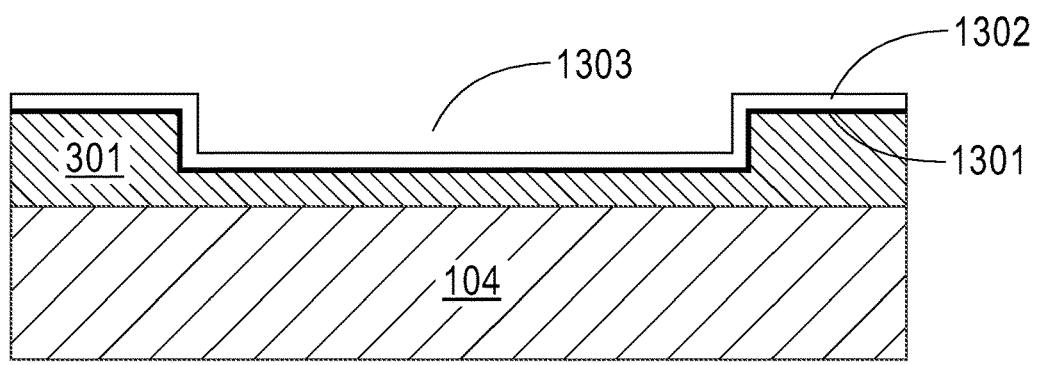
FIG. 13 depicts a sectional view through the plane of FIG. 3 that shows a layer of seed metal deposited over an adhesion metal layer in the cavity shown in FIG. 12 during a fabrication of the anode side of the microbattery in accordance with an embodiment of the present invention.

FIG. 13 shows a next step in which an adhesion metal layer 1301 and a layer of seed metal 1302 are deposited as a layer in cavity 303 creating layered cavity 1303 and over a surface of bottom polymer flex substrate 301. In an embodiment, adhesion metal layer 1301 is titanium tungsten (TiW), however, those skilled in the art understand that titanium (Ti) or tantalum (Ta) or other suitable material can be used in place of TiW. In an embodiment, adhesion metal layer 1301 serves as a metal barrier to prevent electrolyte egress from the anode of the battery. In an embodiment seed metal 1302 is copper (Cu), however, those skilled in the art understand that seed metal 1302 may be another appropriate material such as gold (Au). Seed metal 1302 serves as an anode current collector. In an embodiment, adhesion metal layer 1301 serves as an electrical contact to the battery. In an embodiment, adhesion metal layer 1301 has discontinuities to electrically isolate a mechanical seal bonded to adhesion metal layer 1301 from a battery electrical circuit.

Figure 14:
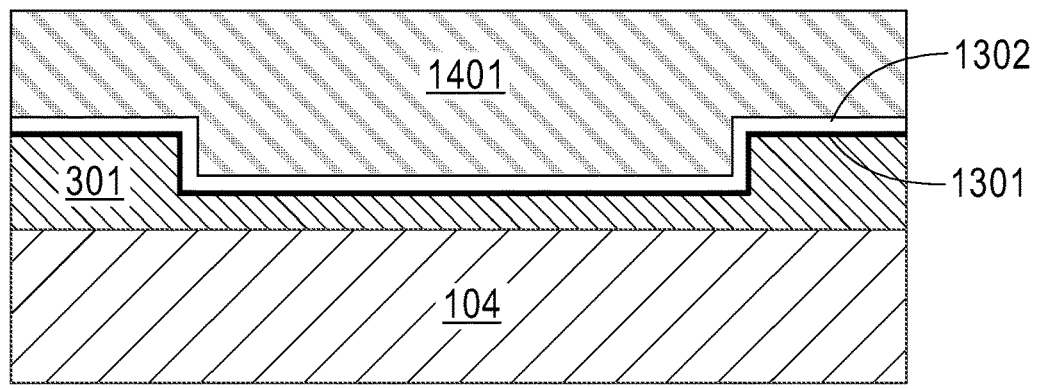
FIG. 14 depicts a sectional view through the plane of FIG. 3 that shows a layer of photoresist deposited over the seed metal in the cavity shown in FIG. 13 during a fabrication of the anode side of the microbattery in accordance with an embodiment of the present invention.

FIG. 14 shows a next step in a fabrication of the anode in which a layer of photoresist 1401 is deposited over seed metal 1302, completely fills layered cavity 1303 and forms a layer of photoresist 1401 over bottom polymer flex substrate 301.

Figure 15:
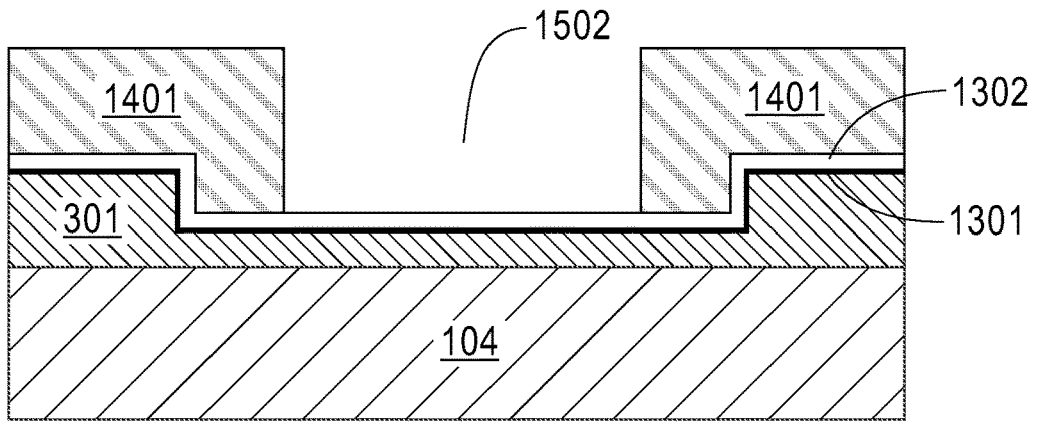
FIG. 15 depicts a sectional view through the plane of FIG. 3 after a photoresist material is applied and developed, exposing the seed metal, the anode current collector, during a fabrication of the anode side of a microbattery in accordance with an embodiment of the present invention.

FIG. 15 shows a next step in a fabrication of the anode in which photoresist 1401 is photopatterned into a shape exposing a surface of seed metal 1302 at the bottom of cavity 1502. Seed metal 1302 is the anode current collector.

Figure 16:
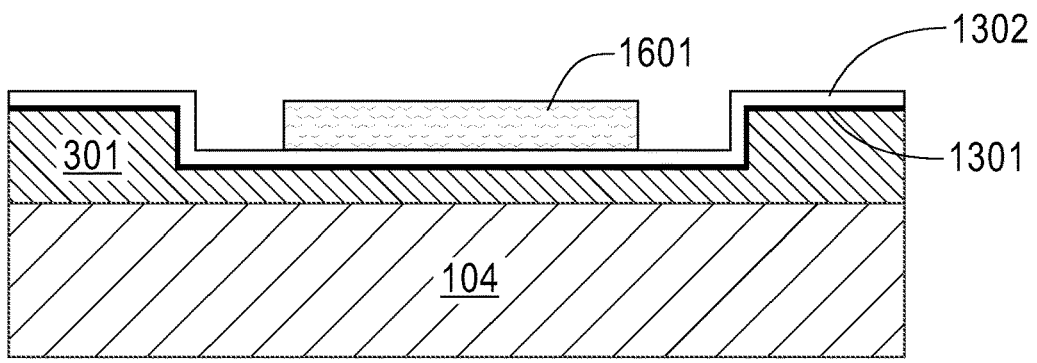
FIG. 16 depicts a sectional view through the plane of FIG. 3 after the seed metal is electroplated with a homogeneous solid composed of indium, bismuth, and zinc to form the anode, during a fabrication of the anode side of a microbattery in accordance with an embodiment of the present invention.

FIG. 16 shows a next step in a fabrication of the anode in which the exposed surface of seed metal 1302 is electroplated with a homogeneous solid composed of indium, bismuth, and zinc (In/Bi/Zn) to form anode material 1601. In an embodiment, anode material 1601 is a homogeneous solid metallic alloy composed of 100 ppm to 1000 ppm Bi, 100 ppm to 1000 ppm In, and the remainder is Zn, however, those skilled in the art understand that anode can be composed of another material, such as zinc metal. An analytical technique such as Proton Induced X-ray Emission (PIXE) can be used to empirically determine the amount of Bi, In, and Zn used in the anode. In an embodiment, anode material 1601 is 1 μm to 50 μm thick, however, those skilled in the art understand that anode material 1601 can be another appropriate thickness. The remainder of photoresist 1401 is removed after anode material 1601 is electroplated on the exposed surface of seed metal 1302.

In an embodiment of the present invention, anode material 1601 is electroplated in a bath in an electroplating tank that contains In in a concentration in a range of 100 ppm to 1000 ppm, Bi in a concentration in a range of 100 ppm to 1000 ppm, with In in a nominal concentration of 300 ppm+/−200 ppm and Bi in a nominal concentration of 300 ppm+/−200 ppm, and Zn. In an embodiment of the present invention, the electroplating tank has sufficient convection to keep the electroplated composition of anode material 1601 uniform independent of its thickness and/or the current used in the electroplating process. The current used electroplating process is pulsed to keep the electroplated composition of anode material 1601 uniform independent of its thickness.

In another embodiment, the component elements of anode material 1601 are electroplated on the exposed surface of seed metal 1302 in separate layers, one component element per layer, in separate electroplating steps and then the separate layers are annealed to create a single homogeneous layer.

Figure 17:
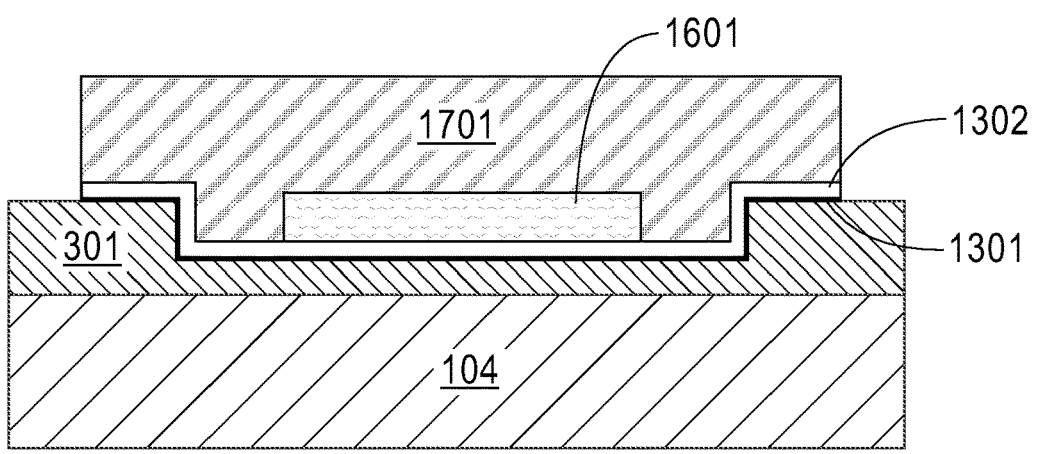
FIG. 17 depicts a sectional view through the plane of FIG. 3 after a layer of photoresist is deposited over the seed metal and the anode during a fabrication of the anode side of a microbattery in accordance with an embodiment of the present invention.

FIG. 17 shows a next step in a fabrication of the anode in which a layer of photoresist 1701 is deposited over seed metal 1302 and anode material 1601 protecting anode material 1601. A patterning of photoresist 1701 defines wiring trace 310 and wiring trace 314 and a pattern of seed metal 1302 and adhesion metal layer 1301. In a subtractive etching process, unmasked areas of seed metal 1302 and adhesion metal layer 1301 are removed. In other embodiments, a plurality of wiring traces are defined to meet a requirement of microsystem 600.

Figure 18:
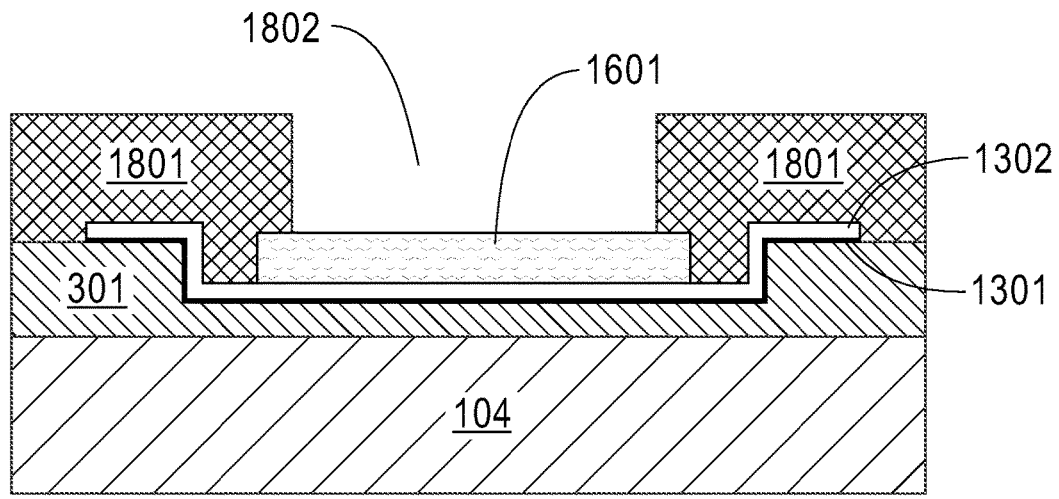
FIG. 18 depicts a sectional view through the plane of FIG. 3 after a layer of polymer bondable seal material is applied and patterned, exposing the surface of the anode during a fabrication of the anode side of a microbattery in accordance with an embodiment of the present invention.

FIG. 18 shows a next step in a fabrication of the anode in which photoresist 1701 is completely stripped and polymer bondable seal material 1801 is applied and patterned, creating cavity 1802 and exposing a surface of anode material 1601. Polymer bondable seal material 1801 that is left after creating cavity 1802 is permanent and is not stripped. Polymer bondable seal material 1801 is polymer bondable seal material 302 of FIG. 3 viewed from a different perspective.

Figure 19:
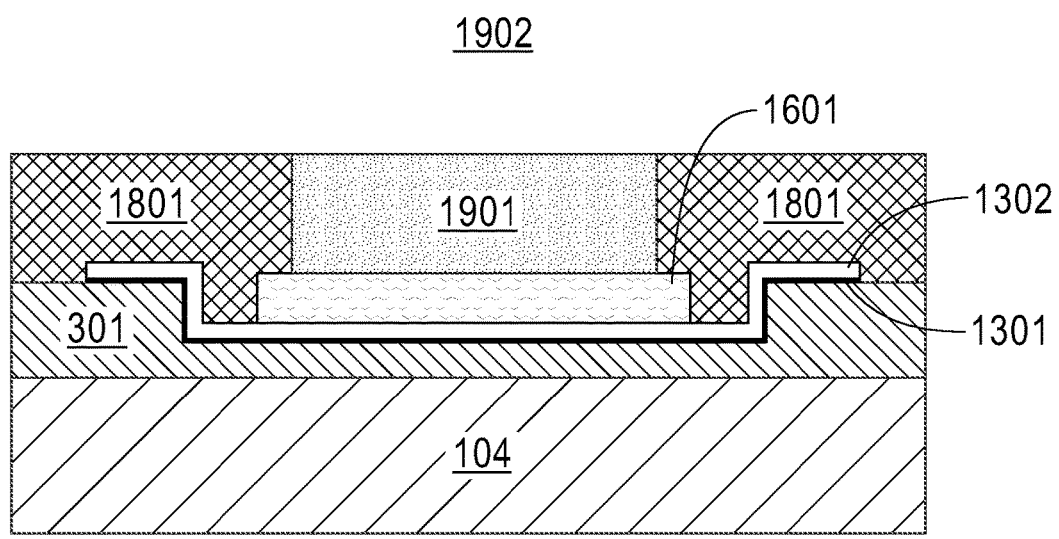
FIG. 19 depicts a sectional view through the plane of FIG. 3 after an electrolyte separator material is deposited into the cavity in FIG. 18 during a fabrication of the anode side of a microbattery in accordance with an embodiment of the present invention.

FIG. 19 shows a next step in a fabrication of the anode in which electrolyte separator material 1901 is deposited into cavity 1802 forming anode side 1902 of the microbattery. In an embodiment, electrolyte separator material 1901 is soaked in an electrolyte, in a wet assembly. In an embodiment, the electrolyte has a pH in a range of 3 to 7. In an embodiment, the electrolyte is one or more of: ammonium chloride, an aqueous salt solution such as KOH, zinc chloride, or zinc acetate with an additive such as ZnO. In an embodiment, electrolyte separator material 1901 is treated to render electrolyte separator material 1901 hydrophylic so that electrolyte separator material 1901 can be filled with electrolyte through a fill port, in a dry assembly. In an embodiment, electrolyte separator 1901 comprises one or more of a flexible porous material, a gel, a sheet that is from 10 μm to 100 μm in thickness that is composed of cellulose, cellophane, polyvinyl acetate (PVA), PVA/cellulous blends, polyethylene (PE), polypropylene (PP), or a mixture of PE and PP.

Having described embodiments of an anode that is an electroplated homogeneous solid metallic alloy (which are intended to be illustrative and not limiting), it is noted that modifications and variations may be made by persons skilled in the art in light of the above teachings. It is therefore to be understood that changes may be made in the particular embodiments disclosed which are within the scope of the present invention as outlined by the appended claims.

Embodiments of the present invention recognize that, in a thin-film microbattery, an electroplated anode has many advantages over an anode composed of a mixture of particles that may be in the form of a paste, for example. The smallest dimension of a structure composed of a mixture of particles is limited to the size of the largest particle in the mixture. For example, if the diameter of the largest particle is about 25 microns, a typical size of a particle in a metallic powder, a minimum anode thickness of about 25 microns is potentially possible with a material that incorporates the particle, if constraints imposed by a fabrication process are not taken into account.

Embodiments of the present invention can achieve a thickness of 1 micron for anode material 1601, an electroplated homogeneous solid metallic alloy. Therefore the minimum patternable line width of the electroplated homogeneous solid metallic alloy is 1 micron or less, which facilitates its use in microbatteries and micro-miniaturized devices. Embodiments of the present invention recognize that common fabrication techniques (e.g., screening, stenciling, and printing) employed to form a structure using particle-based material incorporating particles 25 microns in size, limit a minimum dimension of the material to something greater than 100 microns.

In addition to being patternable down to a 1 micron dimension, the electroplated homogeneous solid metallic alloy has essentially no porosity, increasing its density and efficiency as it contains no wasted space. In one embodiment, the percentage of voids by volume in the electroplated homogeneous solid metallic alloy is less than 0.01%, preferably 0%. It is denser than a particle-based material that often contains voids, conductivity-enhancing additives, and binder additives that envelope the particles to hold them in place in a battery. Because of its density, the electroplated homogeneous solid metallic alloy can be plated to an essentially mirror smooth surface, whereas the smoothness of a particle-based material is defined by the sizes of the particles that it contains. In one embodiment, the proportions of the constituent components in anode material 1601 are homogeneous to the degree that the proportion of any constituent component (In, Bi, Zn) within a volume defined within the anode material, such as film height of anode material (in mm) cubed, deviates by less than 10% from the bulk proportion of that constituent component in the total volume of the anode material.

Embodiments of the present invention recognize that anode material 1601 is more volume-efficient than a particle-based material as the entirety of its mass participates in its function whereas only a portion of the total mass of the material composed of a mixture of particles participates in its function. Therefore a material with low or no porosity is advantageous in a microbattery. The size of a microbattery is a significant factor in determining whether a use of the battery is practical in an application or in a given physical environment.

In an embodiment, anode material 1601 is a homogeneous solid metallic alloy composed of 100 ppm to 1000 ppm Bi, 100 ppm to 1000 ppm In, and the remainder is Zn and because it is a continuous film, its resistivity is close to that of bulk zinc which is about $5 \times 10^{-8}$ to $6 \times 10^{-8}$ ohm-m. The resistivity of a zinc paste composed of particles is about $10000 \times 10^{-8}$ ohm-m, which is about a 2000 fold increase in resistivity over that of anode material 1601. Embodiments of the present invention recognize that an anode material with a low resistivity is advantageous in a microbattery because the resistivity of the anode material contributes to the internal resistance of the microbattery. The greater a battery's internal resistance is, the slower the battery is in providing pulses of current to a load, i.e., the rise time of a current pulse increases as the internal resistance increases. Therefore for a microbattery that is required to provide significant pulses of current, a continuous film anode material is better than a porous paste approach that uses a particle-based material. In an embodiment, the surface the exposed surface of seed metal 1302 is textured so that electroplated anode material 1601 is textured to increase its surface area to enhance its ability to provide large current draws.

In addition, the homogeneous solid metallic alloy of anode material 1601 is mechanically stronger than that of a particle-based paste. The strength of anode material 1601 is about 100 MPa while that of a particle-based paste is at least 1000 times lower. The strength of an anode material contributes to the physical robustness of a microbattery. Because anode material 1601 is electroplated to seed metal 1302, the interface between seed metal 1302 and anode material is exceptionally strong, while the anode/current collector interface of a particle-based paste anode material is relatively weak and contact between the anode and the current collector is predominately maintained only by forces external to the interface. In a flexible microbattery, the interface between anode material 1601 and seed metal 1302 is unlikely to crack or delaminate under flexing while that of a particle-based anode material is much more apt to crack or delaminate under flexing.

The homogeneous solid metallic alloy of anode material 1601 may interface with a variety of electrolytes (e.g., alkaline (KOH), zinc acetate, zinc chloride, and ammonium chloride) without a need to reformulate a mixture of the components of anode material 1601. Because a particle-base paste requires a binder to hold its constituent particles together, the characteristics of a chemical reaction at the binder/electrolyte contact interface must be carefully considered when selecting appropriate materials, as only specific binders can work with a specific electrolyte and vise versa, making the design and development of such a structure relatively involved compared to that of homogeneous solid metallic alloy of anode material 1601.

Another consideration in a development of a particle-based paste anode is that of an optimization of the relative quantities of the binder, conductivity enhancers, and the constituent particles is the paste, and optimizing the solvent that is used during screening, stenciling, or printing of the paste. Tradeoffs must be made between resistivity and mechanical properties of the paste, and flow enhancers that fabrication techniques may require during construction of particle-based paste anode. Anode material 1601 is optimized in situ so no optimization or tradeoffs are required during its development, and since it is not a paste, no solvent is necessary to enhance its handling characteristics during fabrication.

Figure 20:
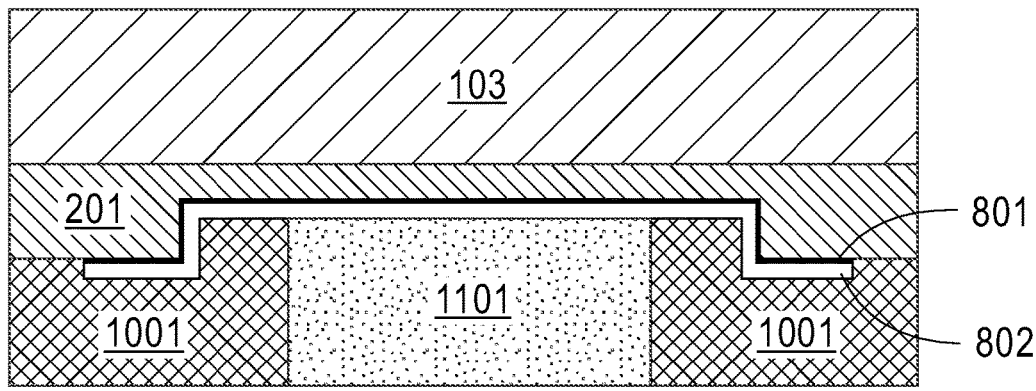
FIG. 20 depicts a sectional view through the plane of FIG. 3 for the anode side and through the plane of FIG. 2 for the cathode side as the cathode side and the anode side are bonded together during a fabrication of the microbattery in accordance with an embodiment of the present invention.
Figure 20:
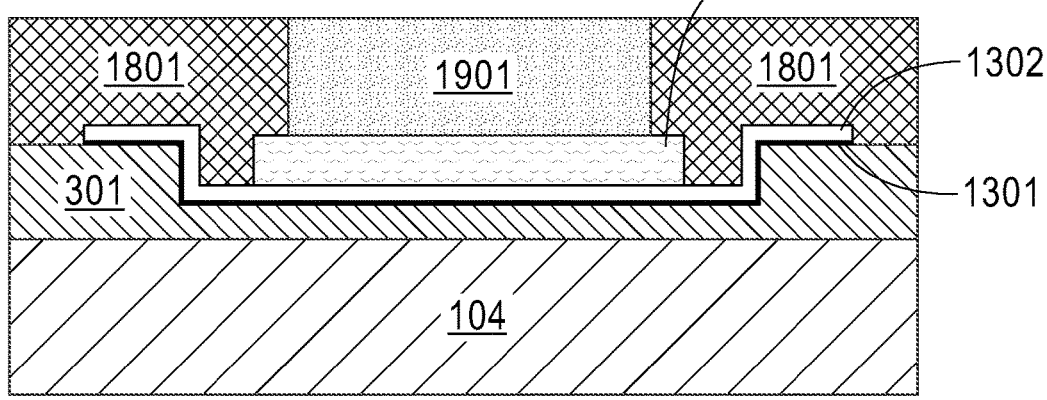

FIG. 20 shows a next step in a fabrication of the microbattery in which cathode side 1102 is bonded with anode side 1902 to from a battery. Temporary support wafers 103 and 104 are a part of microbattery fabrication structure 2001 and are removed in a next step in a fabrication of the microbattery. In an embodiment, the anode side and the cathode side of the microbattery are fabricated in parallel. FIG. 1 also depicts a joining of microassembly top planar 101 with microassembly bottom planar 102 such that the two sides of the microbattery would be joined together. In an embodiment, the two sides of the microbattery are hermetically joined and sealed together.

Figure 21:
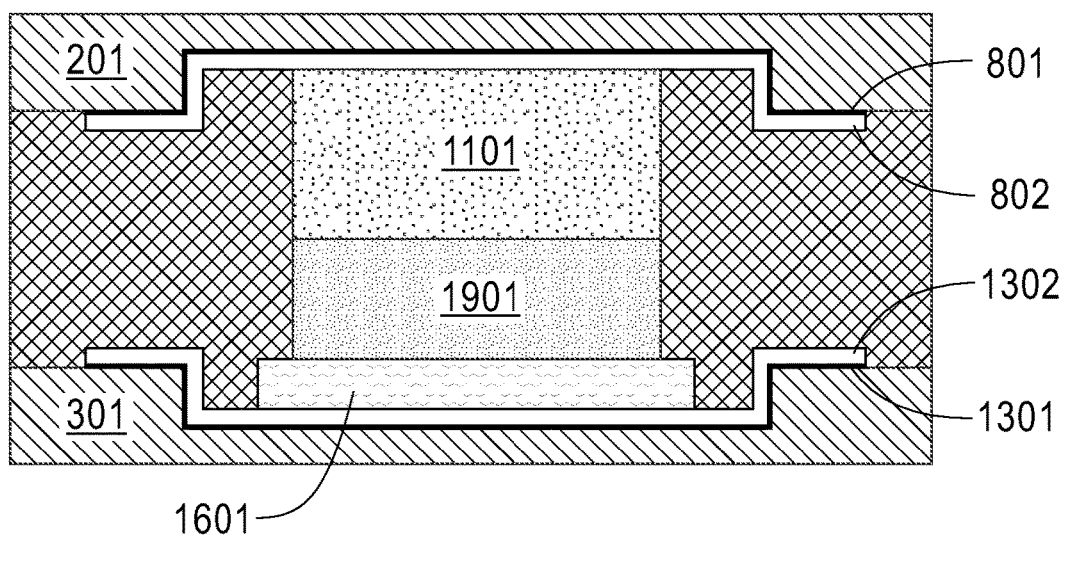
FIG. 21 depicts a sectional view after the cathode side and the anode side are bonded together to complete a fabrication of the microbattery in accordance with an embodiment of the present invention.

FIG. 21 shows completed microbattery 2102 after temporary support wafers 103 and 104 are removed from battery fabrication structure 2001. Electrolyte separator material 1901 is in direct contact with cathode material 1101. In an embodiment temporary support wafers 103 and 104 are removed via one or more laser cuts.

In an embodiment, a thickness of microbattery 2102 is no greater than about 150 µm. In an embodiment, microbattery 2102 has a volume less than 1 cubic mm. In an embodiment, microbattery 2102 has a flexibility defined by a radius of curvature of between about 4 mm and 20 mm. In an embodiment, microbattery 2102 has metal or dielectric coating applied to an exterior plane and/or an end surface of one or more of a surface or substrate and/or adhesive join on microbattery 2102 to create a sealing layer to prevent electrolyte egress. In an embodiment, microbattery 2102 produces an open circuit voltage of between 1.4V and 1.8V and has a discharge capacity of between 10 uA-hours and 200 uA-hours. In an embodiment, microbattery 2102 has a total cavity volume of less than 1 cubic millimeters. In an embodiment, microbattery 2102 is less than 200 µm thick. In an embodiment, microbattery 2102 powers silicon die 206 and/or silicon die 306. In an embodiment, microbattery 2102 powers one or more silicon dies that are substantially similar to silicon die 206 or silicon die 306.

Figure 22:
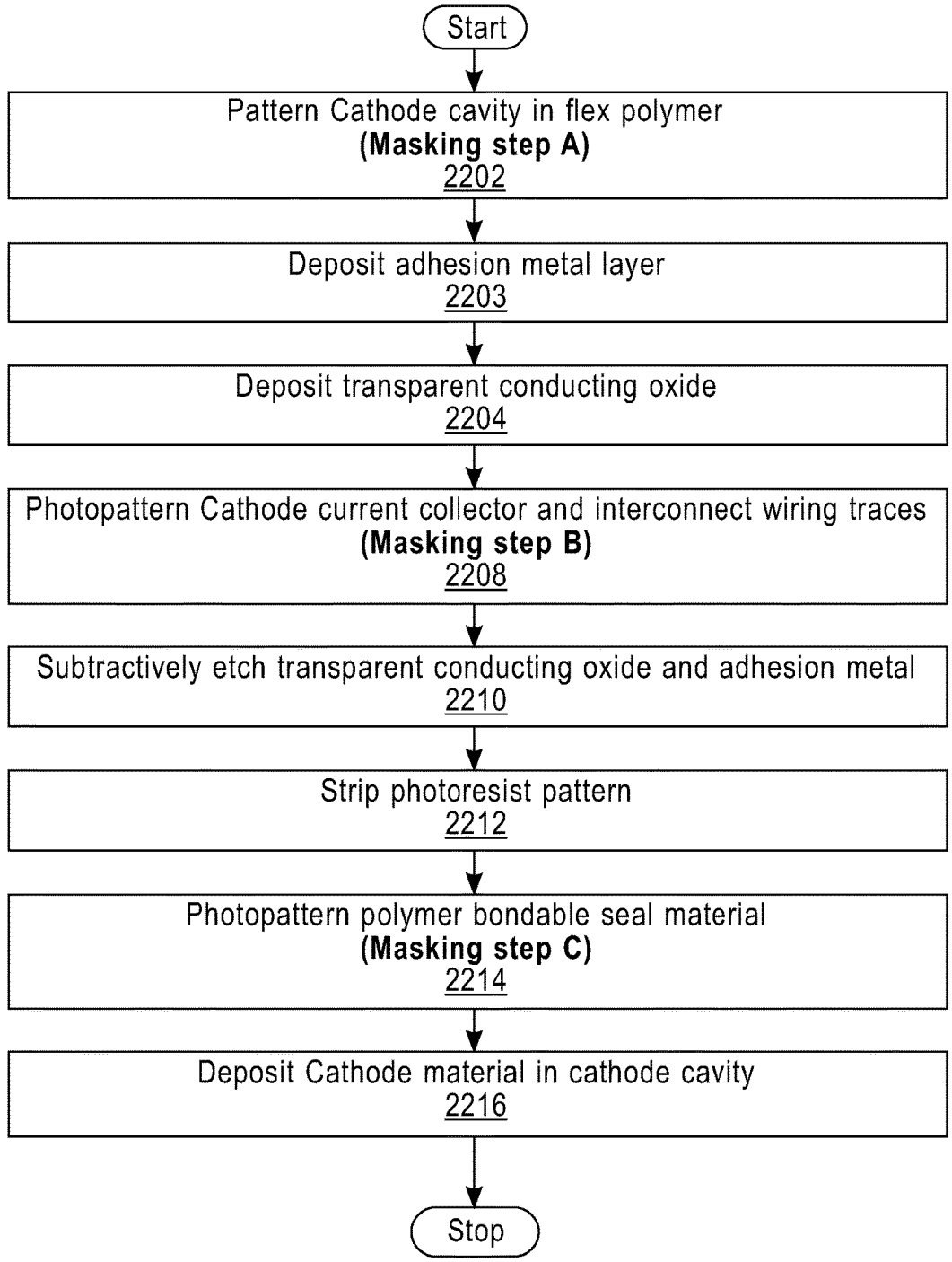
FIG. 22 is a flowchart depicting fabrication steps of a cathode side of a microbattery in accordance with an embodiment of the present invention.

FIG. 22 depicts the steps of a flowchart for a process of forming cathode side 1102 of microbattery 2102.

The first step in this exemplary process flow is to etch cavity 203 into top polymer flex substrate 201 (step 2202) to accommodate a construction of a cathode of microbattery 2102 (e.g., by laser processing). The process of etching cavity 203 uses a first mask in the process. Subsequent to etching cavity 203, adhesive metal layer 801 (e.g., titanium tungsten) is deposited into cavity 203 (step 2203) and transparent conducting oxide 802 (e.g., indium tin oxide) is deposited on adhesive metal layer 801 in cavity 203 (step 2204). Subsequent to depositing transparent conducting oxide 802, photoresist 901 is deposited over transparent conducting oxide 802 and is photopatterned using a second mask in the process (step 2208). Areas of unmasked transparent conducting oxide 802 and adhesive metal layer 801 are subtractively etched to create interconnect wiring trace 210 and 214 (step 2210). In a subtractive etching process, unmasked areas of a material are removed.

Subsequent to creating cavity 1002, the photoresist pattern created in step 2208 is stripped (step 2212) and, using a third mask in the process, polymer bondable seal material 1001 (polymer bondable seal material 202 and 213) is applied and photopatterned (step 2214) creating cavity 1002. Cathode material 1101 is inserted into cavity 1002 (step 2216) to complete the construction of the cathode side of microbattery 2102 (step 2216).

Figure 23:
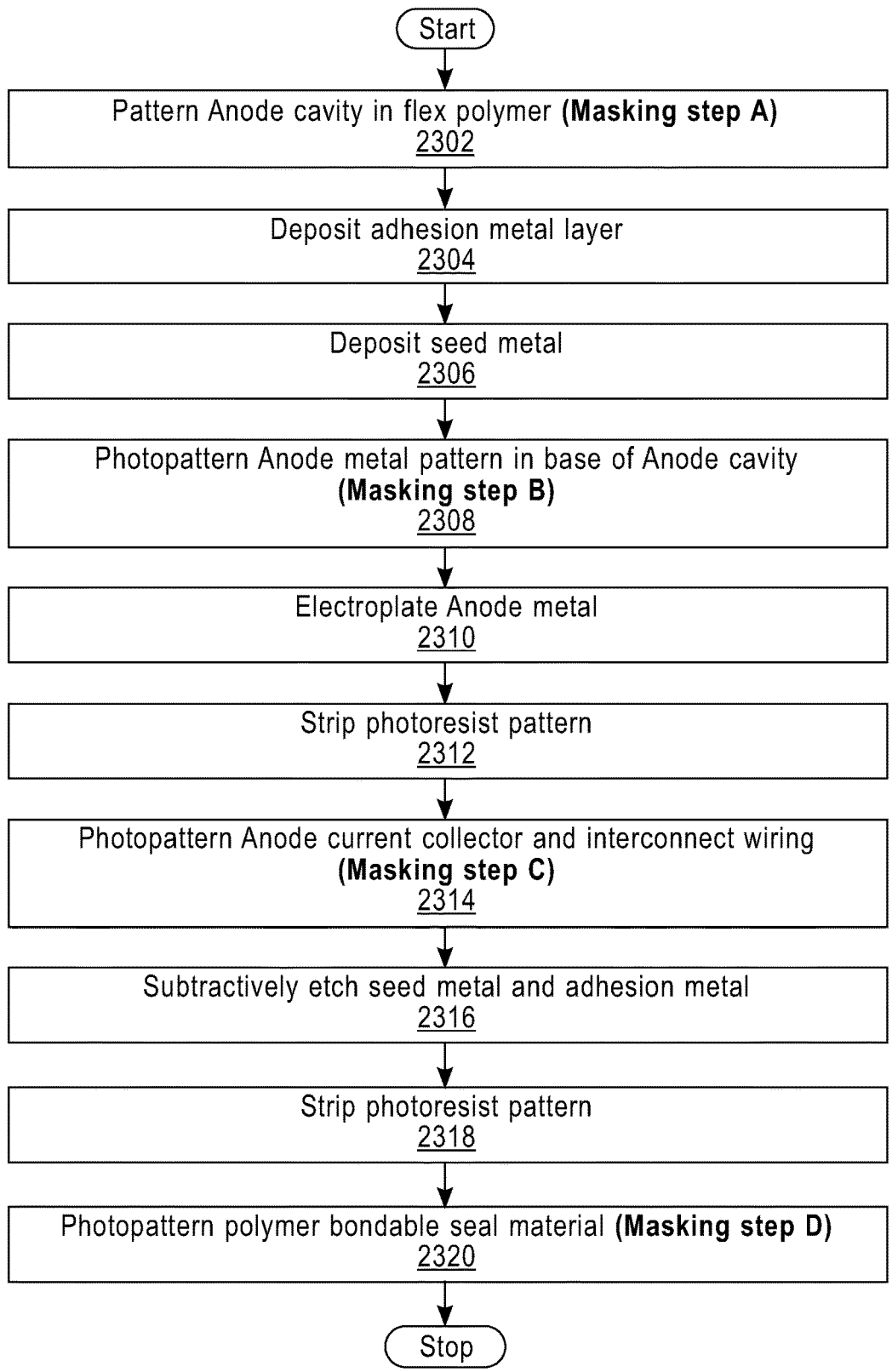
FIG. 23 is a flowchart depicting fabrication steps of an anode side of a microbattery in accordance with an embodiment of the present invention.

FIG. 23 depicts the steps of a flowchart for a process of forming anode side 1902 of microbattery 2102.

The first step in this exemplary process flow is to etch cavity 303, using a first mask in the process, into bottom polymer flex substrate 301 (step 2302) to accommodate a construction of an anode of microbattery 2102 (e.g., by laser processing). Adhesion metal layer 1301 (e.g., titanium tungsten) is deposited in cavity 303 (step 2304) and seed metal 1302 (e.g., copper) is deposited on adhesion metal layer 1301 in cavity 303 to create cavity 1303 (step 2306). Subsequent to depositing seed metal 1302 in cavity 303, deposit photoresist 1401 over seed metal 1302 to completely fill cavity 1303 and form photoresist 1401 over bottom polymer flex substrate 301. Using a second mask in the process, photopattern photoresist 1401 to create cavity 1502 to expose surface of seed metal 1302, the anode current collector (step 2308). The surface of seed metal 1302 is electroplated with a homogeneous solid to form anode material 1601 (step 2310). In an embodiment anode material 1601 is zinc. In another embodiment anode material 1601 is a homogeneous solid metallic alloy comprising 100 ppm to 1000 ppm Bi and 100 ppm to 1000 ppm In, and a remainder is Zn. The remainder of photoresist 1401 is stripped (step 2312).

Photoresist 1701 is deposited over seed metal 1302 and anode material 1601 to form a layer of photoresist 1701 over anode material 1601 and seed metal 1302. A patterning of photoresist 1701 defines wiring trace 310 and wiring trace 314 and a pattern of seed metal 1302 and adhesion metal layer 1301 (step 2314). In a subtractive etching process, unmasked areas of seed metal 1302 and adhesion metal layer 1301 are removed (step 2316). In other embodiments, a plurality of wiring traces are defined to meet a requirement of microsystem 600. The remainder of photoresist 1701 is stripped (step 2318). Using a forth mask in the process, polymer bondable seal material 1801 (polymer bondable seal material 302 and 313) is applied and photopatterned to create cavity 1802 (step 2320). Electrolyte separator material 1901 is deposited into cavity 1802 forming anode side 1902 of the microbattery, completing the construction of anode side 1902 of microbattery 2102 (step 2320).

Figure 24:
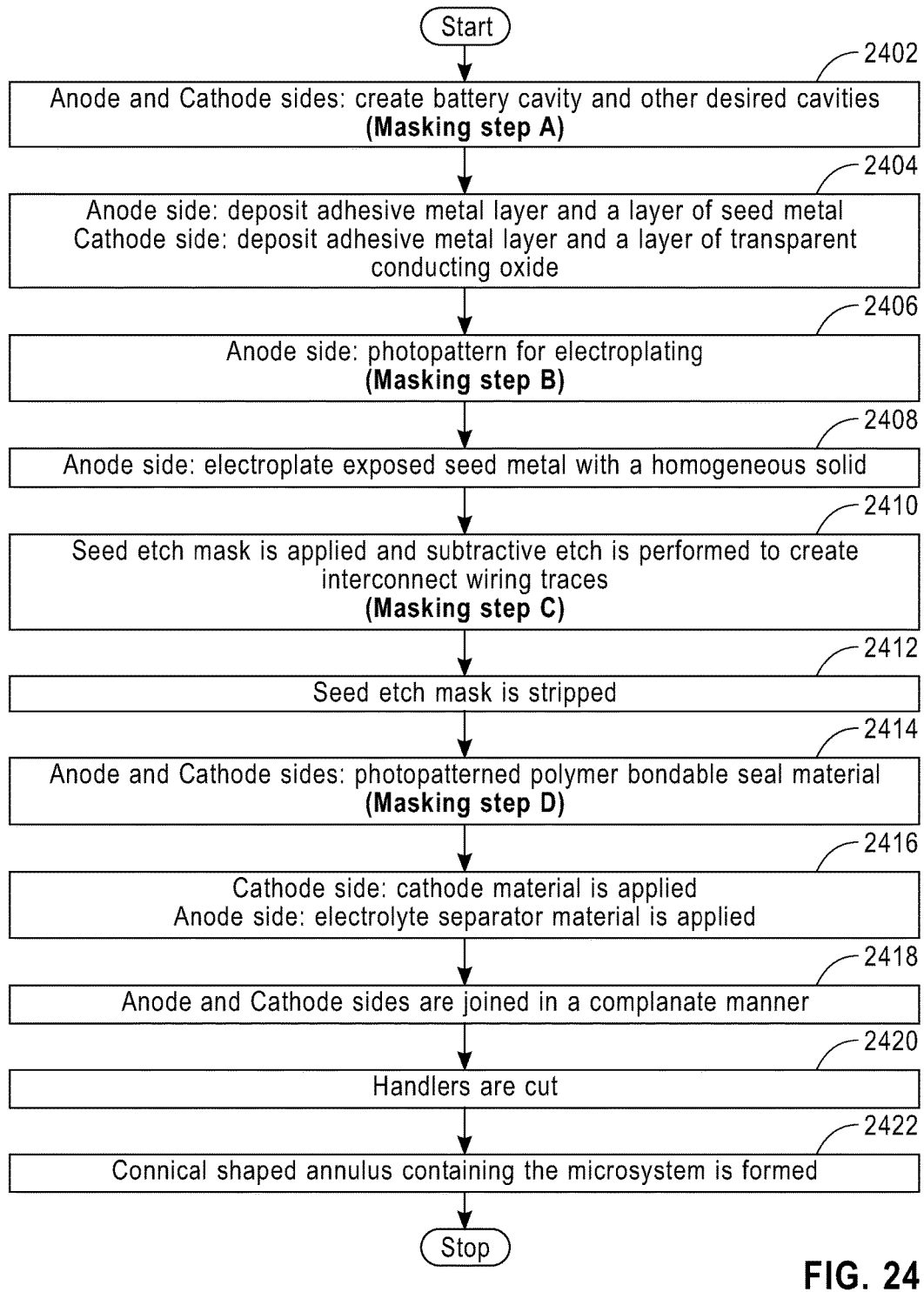
FIG. 24 is a flowchart depicting fabrication steps of a microsystem containing a microbattery in accordance with an embodiment of the present invention.

FIG. 24 depicts the steps of a flowchart for a process of forming microsystem 600 that includes microbattery 2102.

The first step in this exemplary process flow is to mask and etch cavity 203 and cavity 303 into top polymer flex substrate 201 and bottom polymer flex substrate 301 respectively, to accommodate a construction of a cathode in cavity 203 and an anode in cavity 303 (step 2402). In an embodiment, cavity 212 and cavity 312 accommodate protuberances from the anode side and the anode side of microsystem 600 and are also etched in step 2402. In other embodiments, one or more other cavities are created on the cathode and/or anode sides of microsystem 600 to accommodate necessary system components. In an embodiment, the mask used in step 2402 is the first mask used in the exemplary process to form microsystem 600.

On the cathode side, an adhesion metal layer 801 and a layer of transparent conducting oxide 802 are deposited in cavity 203 (step 2404). On the anode side, adhesion metal layer 1301 and a layer of seed metal 1302 are deposited in cavity 303 (step 2404).

The anode side is masked and photopatterned to create cavity 1502 and expose a surface of seed metal 1302 in preparation for electroplating the surface (step 2406). In an embodiment, the mask used in step 2406 is the second mask used in the exemplary process to form microsystem 600. The exposed surface of seed metal 1302 is electroplated with a homogeneous solid composed of indium, bismuth, and zinc (In/Bi/Zn) to form anode material 1601 (step 2408).

A seed etch mask is applied to the anode side (photoresist 1701) and the cathode side (photoresist 901) and a subtractive etch is performed to create interconnect wiring traces 310 and 314 on the anode side and interconnect wiring traces 210 and 214 on the cathode side (step 2410). In other embodiments, one or more other appropriate wiring traces are created to distribute signals and power on microsystem 600. In an embodiment, the mask used in step 2410 is the third mask used in the exemplary process to form microsystem 600.

In an embodiment, the seed etch mask applied in step 2410 is stripped from the anode side and the cathode side, exposing the electroplated anode (anode material 1601) on the anode side and transparent conducting oxide 802 on a floor of 1002 on the cathode side (step 2412). In an embodiment, transparent conducting oxide 802 is indium tin oxide (ITO).

Polymer bondable seal material is applied and photopatterned, creating polymer bondable seal material 202 and 213 on the cathode side and creating polymer bondable seal material 302 and 313 on the anode side (step 2414). In an embodiment, the mask used in step 2414 is the fourth mask used in the exemplary process to form microsystem 600. Cathode material 1101 is applied to and fills cavity 1002 on the cathode side and electrolyte separator material 1901 is deposited into cavity 1802 on the anode side (step 2416). In an embodiment, cathode material 1101 is manganese dioxide (MnO2), however, those skilled in the art understand that other suitable materials can be used.

The anode side and the cathode side are conjoined (step 2418). A first handler is removed (temporary support wafer 103), and the outlines of microsystem 600 is laser cut, and then a second handler (temporary support wafer 104) is removed (step 2420), creating "C" shaped microsystem 500. Those skilled in the art know that the order in which temporary support wafer 103 and temporary support wafer 104 are removed is immaterial to the present invention. An opening in "C" shaped microsystem 500 is closed by a bonding of rabbet joint adhesive 308 on microsystem bottom component 105 with rabbet joint adhesive 208 on microsystem top component 106 (step 2422). In an embodiment, a fabrication process of microsystem 600 completes in step 2422.

The embodiments of the invention described herein employ photolithographic fabrication techniques, but those skilled in the art know that other fabrication techniques can be used to fabricate microsystem 600, such as electron beam lithography, scanning probe lithography, and particle lithography among other techniques.

What is claimed is:

1. A method for forming a battery, the method comprising:
   fabricating a cathode side including a cathode material located in a cathode cavity formed in a first dielectric element;
   fabricating an anode side including an anode material located in an anode cavity formed in a second dielectric element; and
   joining the cathode side and the anode side in a complanate manner, wherein the fabricating the cathode side uses no more than two lithographic masks and comprises:

forming an adhesion metal layer in the cathode cavity and on a topmost surface of the first dielectric element;

forming a transparent conductive oxide layer on the adhesion metal layer; and removing end portions of the transparent conductive oxide and the adhesion metal layer that are present on the topmost surface of the first dielectric element.

2. The method of claim 1, wherein the fabricating the anode side comprises using no more than three lithographic masks.

3. The method of claim 1, wherein the removing the end portions of the transparent conductive oxide and the adhesion metal layer comprises a subtractive photolithographic technique.

4. The method of claim 1, further comprising:

forming polymer bondable seal material portions on portions of the transparent conductive oxide layer, while maintaining a surface of the transparent conductive oxide layer that is located within the cathode cavity physically exposed.

5. The method of claim 4, further comprising:

forming the cathode material in the cathode cavity and directly contacting the physically exposed surface of the transparent conductive oxide.

6. The method of claim 2, wherein the fabricating the anode side comprises:

forming an adhesion metal layer in the anode cavity and on a topmost surface of the second dielectric element;

forming a seed metal layer on the adhesion metal layer;

forming the anode material on a portion of the seed metal layer that is located in the anode cavity; and removing end portions of the seed metal layer and adhesion metal layer that are present on the topmost surface of the second dielectric element.

7. The method of claim 6, wherein the end portions of the seed metal layer and adhesion metal layer comprises a subtractive photolithographic technique.

8. The method of claim 6, further comprising:

forming polymer bondable seal material portions on portions of the seed metal layer, while maintaining a surface of the seed metal layer that is located within the anode cavity physically exposed.

9. The method of claim 8, further comprising:

forming electrolyte in the anode cavity and directly contacting the physically exposed surface of the anode material.

10. The method of claim 1, wherein the joining the cathode side and the anode side in a complanate manner comprises bonding polymer bondable seal material portions located in the anode side to bonding polymer bondable seal material portions located in the cathode side.

11. The method of claim 1, wherein the first and second dielectric elements comprise a flexible polymer.

12. The method of claim 1, wherein each of the first and second dielectric elements is present on a handle substrate and each handle substrate is removed after the joining.

13. The method of claim 6, wherein the anode material is a homogeneous solid metallic alloy.

14. The method of claim 13, wherein the homogeneous solid metallic alloy is composed of 100 ppm to 1000 ppm Bi, 100 ppm to 1000 ppm In and the remainder is Zn.

15. A method for forming a battery, the method comprising:

fabricating a cathode side including a cathode material located in a cathode cavity formed in a first dielectric element;

fabricating an anode side including an anode material located in an anode cavity formed in a second dielectric element; and joining the cathode side and the anode side in a complanate manner, wherein the fabricating the anode side uses no more than three lithographic masks and comprises forming an adhesion metal layer in the anode cavity and on a topmost surface of the second dielectric element;

forming a seed metal layer on the adhesion metal layer;

forming the anode material on a portion of the seed metal layer that is located in the anode cavity; and removing end portions of the seed metal layer and adhesion metal layer that are present on the topmost surface of the second dielectric element.

\* \* \* \* \*